(12) United States Patent
Strauss et al.

(10) Patent No.: US 6,335,466 B1
(45) Date of Patent: Jan. 1, 2002

(54) FLUORINATED AMINO POLYHEDRAL BORATE COMPOUNDS

(75) Inventors: Steven H. Strauss; Sergei V. Ivanov, both of Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/704,252

(22) Filed: Oct. 31, 2000

(51) Int. Cl.$^7$ .................................................. C07F 5/02
(52) U.S. Cl. ..................................... 564/9; 568/3; 568/4
(58) Field of Search ............................. 564/9; 568/3, 4

(56) References Cited

U.S. PATENT DOCUMENTS 3,138,602 A * 6/1964 Szymanski et al.
3,526,650 A * 9/1970 Young

OTHER PUBLICATIONS

CA:120:181656 abs of Inorg Chem by Meyer et al 32(23) pp. 5053–7, 1993.*
CA:124:202360 abs of Chem Ber by Roth et al 128(12) pp. 1221–4, 1995.*
CA:128:200029 abs of J Organomet Chem by Callaghan et al 550(1–2) pp. 441–444, 1998.*

* cited by examiner

*Primary Examiner*—Jean F. Vollano
(74) *Attorney, Agent, or Firm*—Townsend and Townsend and Crew LLP

(57) ABSTRACT

This invention provides a compound comprising fluorinated aminoborate monoanion of the formula:

$$[R^1R^2R^3N-B_aH_bF_c]^{-1} \qquad \text{I}$$

methods for preparing the same, and uses thereof, where $R^1$, $R^2$, $R^3$, a, b, and c are those defined herein.

27 Claims, 1 Drawing Sheet

FLUORINATED AMINO POLYHEDRAL BORATE COMPOUNDS

FIELD OF THE INVENTION

This invention relates to compounds comprising a fluorinated aminoborate anion. In particular, the present invention relates to compounds comprising a fluorinated polyhedral aminoborate anion.

BACKGROUND OF THE INVENTION

A compound containing a weakly coordinating anion (i.e., an anion that coordinates only weakly with a cation) is useful in a variety of applications including as an electrolyte and a catalyst. Investigations of reactive metal and nonmetal cations continue to spur the development of new weakly coordinating anions. See, for example, Bochmann, *Angew. Chem., Int. Ed. Engl.* 1992, 31 1181; Strauss, *Chem. Rev.* 1993, 93, 927, Strauss, *Chemtracts-Inorganic Chem.* 1994, 6,1; and Seppelt, *Angew. Chem., Int. Ed. Engl.* 1993, 32, 1025. One of the most important uses of weakly coordinating anions is to enhance the catalytic activity of metal cations. Two examples that have received considerable attention recently are metallocene-catalyzed olefin polymerization, and lithium-catalyzed Diels-Alder reactions and 1,4-conjugate addition reactions. See Turner, European Patent Appl. No. 277,004, 1988; Pellecchia et al., *Makromol. Chem., Rapid Commun.* 1992, 13, 265; DuBay et al., *J. Org. Chem.* 1994, 59, 6898; Saidi et al., *Chem. Ber.* 1994, 127, 1761; Kobayashi et al., *Chem. Lett.* 1995, 307; and Arai et al., *Angew. Chem., Int. Ed. Engl.* 1996,15, 3776.

Useful anions must not only be weakly coordinating, they must also be stable with respect to oxidation and/or fragmentation in the presence of highly electrophilic cations. In addition, an ideal weakly coordinating anion should have a single negative charge dispersed over a large surface composed of relatively nonpolar bonds to weakly basic atoms such as hydrogen or the halogens.

A variety of monoanions have been prepared to meet one or more desirable characteristics described above, including fluorinated carborane monoanion as described in commonly assigned U.S. Pat. No. 6,130,357, issued Oct. 10, 2000, which is incorporated herein by reference in its entirety. However, to date no fluorinated amino derivatives of polyhedral borate compounds (i.e., compounds comprising a fluorinated aminoborate anion) have been made. It is believed that fluorinated aminoborates are particularly useful as the amine functional group can be fuirther derivatized by a variety of groups, thereby allowing potential use in much wider range of applications than other polyhedral borate compounds. In addition, most current weakly coordinating anions (e.g., polyhedral borate anions) are relatively expensive to produce.

Therefore, there is a need for a fluorinated aminoborate anion that is weakly coordinating, and is thermally and hydrolytically stable. There is also a need for a method for relatively inexpensively producing the same.

SUMMARY OF THE INVENTION

This invention provides a compound comprising fluorinated aminoborate monoanion of the formula:

$$[R^1R^2R^3N\text{——}B_aH_bF_c]^{-1} \quad \text{I}$$

where $R^1$, $R^2$, $R^3$, a, b, and c are defined below. In Formula I, $R^1$, $R^2$, and $R^3$ are bonded to N, which in turn is bonded to boron, and each of H and F is bonded to a different boron atom. Each of $R^1$, $R^2$, and $R^3$ is independently selected from the group consisting of hydrogen, $C_1$–$C_{20}$ alky, $C_3$–$C_{10}$ cycloalkyl, $C_6$–$C_{20}$ aryl, $C_7$–$C_{20}$ aralkyl, haloalkyl, alkenyl, polymer, and silyl. Exemplary polymers include polystyrene, polyethylene, polyethylene glycol, polypropylene, polyacrylate, polyurethane, polycarbonate, polytetrafluoroethylene, and other polymeric resins that allow a compound of the present invention to be bound to the polymeinc support. Preferably, each of $R^1$, $R^2$, and $R^3$ is independently selected from the group consisting of hydrogen, methyl, ethyl, butyl, benzyl, hexyl, cyclohexylmethyl, octyl, and dodecyl. The variable a is an integer from 6 to 14, preferably 10 or 12, and more preferably 12. The variable b is an integer from 0 to 12, preferably 0. And the variable c is an integer from 12 to 13, preferably c is a−1 (i.e., when a is 10 or 12, c is preferably 9 or 11, respectively); and the sum of 1+b+c is a.

Since the fluorinated aminoborate monoanion of the present invention is weakly coordinating and is stable under a variety of conditions, it can be formulated into a variety of forms. For example, the compound of the present invention can be dissolved in a variety of solvents to provide solutions which comprise the fluorinated aminoborate monoanion of the present invention. Alternatively, the compound of the present invention can be heated to provide a molten salt or a liquid comprising the fluorinated aminoborate monoanion of the present invention. Or a gel comprising the fluorinated aminoborate monoanion of the present invention can be formulated by admixing the compound of the present invention with appropriate polymer or by admixing the compound of the present invention with the polymer's precursor prior to a polymerization reaction.

Another embodiment of the present invention is a method for producing a compound comprising fluorinated aminoborate monoanion of Formula I above. Thus, the method of the present invention replaces at least one of the non-fluorine substituent on the boron atom with fluorine.

The compound of the present invention provides a multiple advantages including stability in a variety of thermal or chemical conditions. The fluorinated aminoborate monoanion of Formula I of the present invention is a weakly coordinating monoanion. Thus, the fluorinated aminoborate monoanion of Formula I can be used in a variety of applications including as an activator for catalysts, and as an electrolyte in batteries. These and other advantages will be readily apparent to those skilled in the art, based on the disclosure contained herein.

DEFINITIONS

The term "hydrocarbyl" refers to a compound having at least one carbon atom. Such compounds include aryl, alkyl, alkenyl and alkynyl. Moreover, hydrocarbyl can be straight chain, branched, or cyclic. Hydrocarbyl can also be substituted with other non hydrogen or carbon atoms such as halide, oxygen, sulfur, nitrogen or phosphorus.

The term "alkyl" refers to aliphatic hydrocarbons, preferably having one to about twenty carbon atoms, which can be straight or branched chain groups. Alkyl groups optionally can be substituted with one or more substituents, such as a halogen, alkenyl, alkynyl, aryl, hydroxy, alkoxy, carboxy, oxo or cycloalkyl. There may be optionally inserted along the alkyl group one or more oxygen, sulflur or substituted or unsubstituted nitrogen atoms. Exemplary alkyl groups include methyl, ethyl, i-propyl, n-butyl, t-butyl, hexyl, octyl, dodecyl, fluoromethyl, difluoromethyl, trifluoromethyl, chloromethyl, trichloromethyl, and pentafluoroethyl.

The term "aryl" refers to aromatic ring moieties, preferably having five to about twenty ring atoms, including carboaryls, such as mono- and bicyclic aromatic carbocyclic ring moieties; and heteroaryls, such as mono- and bicyclic aromatic heterocyclic ring moieties. Aryl groups can be substituted with one or more substituents, such as a halogen, alkenyl, alkyl, alkynyl, hydroxy, amino, thio, alkoxy or cycloalkyl. Exemplary aryls include pyrrole, thiophene, fuiran, imidazole, pyrazole, 1,2,4-triazole, pyridine, pyrazine, pyrimidine, pyridazine, thiazole, isothiazole, oxazole, isoxazole, s-triazine, benzene, indene, indoline, isoindene, benzofuran, dihydrobenzofuran, benzothiophene, indole, 1H-indazole, azulene, tetrahydroazulene, benzopyrazole, benzoxazole, benzoimidazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benisoxazine.

The term "alkenyl" refers to aliphatic hydrocarbons, preferably of two to about twenty carbon atoms, having one or more double bonds between adjacent carbon atoms. Alkenyl groups can be straight or branched chain groups. Exemplary alkenyl groups include vinyl, 1,3-butadienyl, 2-propenyl, chlorovinyl, fluoroethenyl, and tetrafluoroethenyl.

The term "alkynyl" refers to aliphatic hydrocarbons, preferably of two to about twenty carbon atoms, having one or more triple bonds between adjacent carbon atoms. Alkynyl groups can further contain a straight or branched chain groups. Exemplary alkynyl groups include ethynyl, 2-propynyl, and 1-propynyl.

The terms "halide" and "halogen" are used interchangeably herein and refer to fluoro, chloro, bromo, or iodo substituent. Similarly, the term "haloalkyl" means alkyl substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all alkyl hydrogen atoms are replaced by fluorine atoms.

The term "cycloalkyl" refers to a substituted or unsubstituted saturated monovalent cyclic hydrocarbon groups, preferably having three to about twenty carbon ring atoms. Substituted cycloalkyl group contains one, two or three substituents which are not hydrogen. In particular, the term cycloalkyl includes, for example, cyclopropyl, cyclopentyl, cyclohexyl, and the like.

The term "aralkyl" refers to a moiety of the formula -$R^aR^b$ where $R^a$ is an alkylene group and $R^b$ is an aryl group as defined above, e.g., benzyl, phenylethyl, and the like.

The term "leaving group" has the meaning conventionally associated with it in synthetic organic chemistry, i.e., an atom or a group capable of being displaced by a nucleophile and includes halide (such as chloro, bromo, and iodo groups), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

The term "organometallic single site olefin polymerization catalyst" refers to an organometallic compound comprising a metal which is coordinated to at least one cyclopentadienyl (i.e., Cp) group or its derivative. The metal, preferably a transition metal, is bonded to the cyclopentadienyl ring by electrons moving in orbitals extending above and below the plane of the ring (i.e., π-bond). Exemplary organometallic single site olefin polymerization catalysts include metallocenes. Typically there are three types of metallocenes: (1) dicyclopentadienyl-metals with the general formula $Cp_2M$, (2) dicyclopentadienyl-metal halides with the general formula $Cp_2MX_a$, and (3) monocyclopentadienyl-metal compounds with the general formula $CpMR_b$, where M is a transition metal, X is a halide, a and b are an integer from 1 to 3, and each R is independently CO, NO, halide, alkyl, or other transition metal ligand well known to one skilled in the art such as an imine or a phosphine. In addition, the cyclopentadienyl can be substituted with one or more alkyl groups, such as methyl, ethyl, propyl, isopropyl, hexyl, tert-butyl, neo-pentyl, and the like. Preferably, the metal in a organometallic single site olefin polymerization catalyst is a transition metal, more preferably a late transition metal. Still more preferably, the metal is selected from the group consisting of zirconium, titanium, halfnium, cobalt, nickel, iron, and palladium. Yet still more preferably, the metal is selected from the group consisting of zirconium, palladium, and titanium. And most preferably, the metal is selected from the group consisting of palladium, and titanium.

The term "catalyst system" refers to a combination of a catalyst and a co-catalyst (i.e., activator).

The terms "co-catalyst" and "activator" are used interchangeably herein and refer to a compound or a moiety which increases the catalytic activity of the catalyst.

The term "silyl" refers to a moiety of the formula $R^aR^bR^cSi$—, wherein each of $R^a$, $R^b$, and $R^c$ is independently hydrogen, alkyl, or aryl. Preferably, each of $R^a$, $R^b$, and $R^c$ is independently alkyl or aryl.

DETAILED DESCRIPTION

Figure 1:
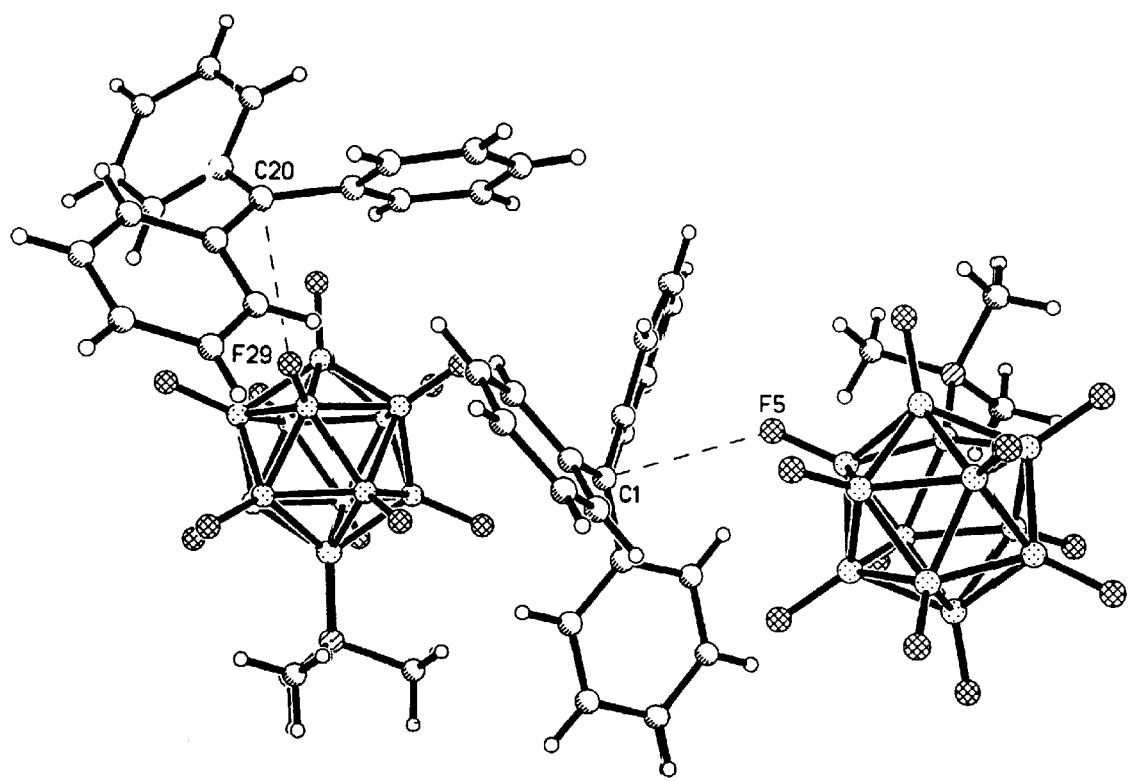
FIG. 1 is an x-ray crystal structure of [$CPh_3$][$Me_3NB_{12}F_{11}$].

The present invention provides a compound comprising fluorinated aminoborate monoanion of the formula:

I

where $R^1$, $R^2$, $R^3$, a, b, and c are those defined above. It should be appreciated that the monoanions of Formula I themselves do not necessarily comprise chemnical compounds. Indeed, in an isolable compound, anions must be paired with cations to maintain electroneutrality. Thus, the actual compound of the present invention is of the formula:

II

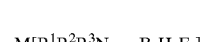

where x is an integer 1 to 4, M is a cation having a valence (i.e., oxidation state) of x, and $R^1$, $R^2$, $R^3$, a, b, and c are those defined above.

M can be any cation including a cation derived from an alkaline metal; alkaline-earth metal; transition metal such as Ag, Zn, Cu, Co, Fe, Mn, Cr, V, Ti, Zr, Rh, Pd, Cd, Hg, Os, Pt, Y, Nb and Mo; lanthanide and actinide series metal; a nitrogen moiety such as ammonium, tetraalkyl ammonium, trialkyl ammonium, dialkyl ammonium, and iminium radical; a phosphorous moiety including tetraalkylphosphonium, and tetraaryl phosphonium. Furthermore, M can be a relatively stable carbocations such as trityl moiety and related carbocations (e.g., $R_3C^+$); sylium cations (e.g., $R_3Si^+$, where each R is independently hydrogen, alkyl or aryl); and other known cations such as hydronium ($H_3O^+$), $H_5O_2^+$, $(Et_2O)_nH^+$, $H_9O_4^+$, and formylium ($HCO^+$), which are known to also coordinate with other polyhedral borate anions. Preferably, the cation is selected from the group consisting of alkaline metal cations, alkaline-earth metal cations, transition metal cations, ammonium, monohydrocarbyl ammonium, dihydrocarbyl ammonium, trihydrocarbyl ammonium, tetra hydrocarbyl ammonium, tetrahydrocarbyl phosphonium, hydronium, formyliumn, silylium cations, and trityl and related carbocations (i.e., substituted trityl carbocations); more preferably from the group consisting of trityl and related carbocations, alkaline metal cations, transition metal cations, monohydrocarbyl ammonium, dihydrocarbyl ammonium, trihydrocarbyl ammonium, silylium cations, and tetrahydrocarbyl ammonium; and most preferably from the group consisting of trityl, triisopropylsilylium, $Li^+$, $Ag^+$, $Tl^+$, $Cs^+$, $Cu^+$, $Cu^{+2}$, monohydrocarbyl ammonium, dihydrocarbyl ammonium, trihydrocarbyl ammonium, and tetra hydrocarbyl ammonium.

When M is a transition metal, it can have one or more ligands (L) including halide such as chloride, bromide and iodide; carbonyl (CO); cyclopentadienyl (Cp) and its derivatives; phosphorous ligand such as trihydrocarbyl phosphine; and other known metal ligands. Preferably a ligand is selected from the group consisting of halides, hydride, carbonyl, cyclopentadienyl and its derivatives, trihydrocarbyl phosphine, hydrocarbyl, nitrosyl, alkoxides, carboxylates, cyanide, cyanate, thiocyanide, thiocyanate and azides; more preferably from the group consisting of carbonyl, halides, hydride, cyclopentadienyl and its derivatives, ammonium, monohydrocarbyl ammonium, dihydrocarbyl ammonium, and trihydrocarbyl ammonium, and trihydrocarbyl phosphonium; and most preferably from the group consisting of carbonyl, halides, cyclopentadienyl and its derivatives, ammonium, monohydrocarbyl ammonium, dihydrocarbyl ammonium, and trihydrocarbyl ammonium.

It will be appreciated that a molar ratio of a cation to the fluorinated aminoborate monoanion of the present invention depends on the valence of the cation. This is reflected in the value x, for example, if the cation is monovalent, e.g., cesium or lithium, then x is 1, and there will be a 1:1 molar ratio between the cation and the fluorinated aminoborate monoanion of the present invention. Whereas if the cation is divalent, e.g., calcium or magnesium, then x is 2, and there will be a 1:2 molar ratio between the cation and the fluorinated aminoborate monoanion of the present invention. Preferably, x is an integer from 1 to 4, more preferably x is 1 to 3, still more preferably x is 1 or 2, and most preferably x is 1.

It should be appreciated that because the fluorinated aminoborate monoanions of the present invention are weakly associating anions; therefore, a cation associated with a fluorinated aminoborate monoanion of Formula I can be readily exchanged with another cation by any of the known methods including ion exchange chromatography and other ion exchange methods.

In accordance with the present invention, one or more of $R^1$, $R^2$, and $R^3$ can also be a polymer. Polymers useful for the present invention are polymers, preferably organic polymers, to which the nitrogen atom of the fluorinated aminoborate monoanion can be attached by a covalent bond. Exemplary polymers usefuil for the present invention include polyethylene glycol, polyethylene, polypropylene, and polystyrene. As used in this invention, a "polymer" can include a linker which links a fluorinated aminoborate monoanion Formula I to the polymeric structure.

The possibility of having a various $R^1$, $R^2$, and $R^3$ substitutions will be evident to one of ordinary skill in the art given the guidance and embodiments disclosed in the present specification. For example, the anion $H_3NB_{12}F_{11}^-$ is a member of a large class of anions. Organic or inorganic groups can be freely substituted and attached to the nitrogen atom instead of the hydrogen group. Indeed, substitution of an organic group, such as a vinyl, allyl, etc. permits the fluorinated aminoborate monoanion to be incorporated into a polymer having commercially important applications as catalysts, conductors, and materials for the separation of anions and/or molecules. A fluorinated aminoborate monoanion such as $H_3NB_{12}F_{11}^-$ and related anions with an $NH_3$ group can readily form a dianion such as $H_2NB_{12}F_{11}^{-2}$ that bind to metal ions through the nitrogen atom. Such dianions are valuable in that one "equivalent" of anionic charge is relatively strongly coordinating, while the second equivalent of an anionic charge is weakly coordinating. Metal complexes incorporating such design are encompassed by the scope of the present invention.

It will be appreciated that since each boron atom of the fluorinated aminoborate monoanion of the present invention has one substituent, the total number of substituents is equal to the total number of boron atoms, i.e., 1+b+c=a.

A compound comprising the fluorinated aminoborate monoanion of the present invention can be used in any industrial applications which requires a stable and/or a weakly coordinating anion. For example, the fluorinated aminoborate monoanion of the present invention can be used as an activator for catalysts, and as an electrolyte in batteries, for example, lithium salts of the fluorinated aminoborate monoanion of the present invention can be used as electrolytes for lithium-based batteries useful in such applications as electric vehicles, cell-phones, and lap-top computers. Compounds comprising the fluorinated aminoborate monoanion are superior co-catalysts (activators) for transition-metal-catalyzed olefin polymerization. There are many other applications as well, ranging from counter-ions for catalysts for organic reactions to counter-ions for polymerization and photoinitiators. There are many other potential commercial uses of the new anions, for example, as a catalyst in chemical reactions such as a catalyst for Diels-Alder reaction and 1,4-conjugate addition reaction.

In one particular aspect of the present invention, compounds comprising a fluorinated aminoborate monoanion of the present invention is used as a catalyst activator. Most conventional olefin polymerization catalyst systems include a constrained geometry catalyst, e.g., a metallocene, and an aluminoxane or some other catalyst activator. See for example, J. Boor *Ziegler-Natta Catalyst and Polymerization*, Academic Press, 1979, New York, and Kaminsky et al., *Adv. Organomet. Chem.*, 1980, 1899. Olefin polymerization catalyst systems comprising a constrained geometry catalyst and an aluminoxane are shown to be highly active in olefin polymerization and capable of forming a stereoregular polymer. For example, laid-open Japanese Patent Publication No. 1-503788 discloses a process for producing a polyethylene of high density or an ethylene/α-olefin copolymer of relatively high density by using a constrained geometry catalyst and an aluminoxane catalyst system at a high pressure and a high temperature. Unfortunately, an aluminoxane cannot be prepared readily or with high reproducibility. Therefore, these catalyst systems and the resulting olefin polymers cannot be produced with satisfactory reproducibility. In addition, aluminoxane is relatively expensive and has to be used in a considerably high ratio relative to the transition metal compound in order to obtain high catalytic activity and stability of polymerization.

Other olefin polymerization catalyst systems include a combination of a constrained geometry catalyst and an ionizing ionic compound. See for example, laid-open Japanese Patent Publication No. 3-207704. Still other olefin polymerization catalyst systems include a catalyst system which is prepared by reacting a halogenated constrained geometry catalyst compound with an organometallic compound and further reacting the resulting product with an ionizing ionic compound. Yet still other olefin polymerization catalyst systems are disclosed in U.S. Pat. No. 6,121,396, issued to Sone et al., which is incorporated herein by reference in its entirety.

In a particularly preferred embodiment of the present invention, the fluorinated aminoborate monoanion is a highly fluorinated aminoborate monoanion that does not strongly bind or associate with positively charged counter cations (i.e., the fluorinated aminoborate monoanion is a weakly coordinating anion). By "highly fluorinated" it is meant that the fluorinated aminoborate monoanion has at least 2 fluorine atoms, preferably at least a/2 fluorine atoms, more preferably at least a-3 fluorine atoms, and most preferably a-1 fluorine atoms, where a is the number of boron atoms as defined above. Without being bound by any particular theory, the weakly coordinating effect is believed to be due to the presence of fluorine atoms, which decrease the effective anion characteristic through, inter alia, an inductive effect. One specific example of a compound comprising the fluorinated aminoborate monoanion of the present invention is [(n-Bu)$_4$N][(cyclohexylmethyl)$_2$HNB$_{12}$F$_{11}$], a structure of which is depicted in FIG. 1. It is believed that the anion consists of an icosahedron of twelve boron atoms with one of the boron atom bonded to the nitrogen atom of the NH(cyclohexylmethyl)$_2$ moiety, and each fluorine atoms are bonded to separate boron atoms.

As stated above, fluorinated aminoborate monoanions of the present invention are weakly coordinating, and as such a compound comprising the fluorinated aminoborate monoanion dissociates readily in a variety of solvents. Thus, a solution comprising the fluorinated aminoborate monoanion of the present invention can readily be prepared by dissolving the compound of the present invention in an appropriate solvent. Suitable solvents include an aqueous solvent; polar and non-polar organic solvents including hexane, pentane, isooctane, chloroform, toluene, benzene, xylene, ether, methylene chloride, ethyl acetate, acetonitrile, tetrahydrofuran, alcohols such as methanol and ethanol, glycols, dimethylsulfoxide, dimethyl formamide, dimethoxy ethane, and carbonate solvents such as propylene carbonate and ethylene carbonate; and a combination thereof.

Another advantage of the compounds of the present invention is that because the anion is weakly coordinating they are highly soluble in most all solvents including weakly basic solvents. Thus, the cation which is associated with the fluorinated aminoborate monoanion of the present invention is generally more reactive than the reactivity of the same cation which is associated to some other anion known to one skilled in the art.

In another embodiment, fluorinated aminoborate monoanions of the present invention can be formulated as a gel by mixing the compound of the present invention with an appropriate polymer using any of the known polymer gel preparation methods. For example, most of the solvent can be removed from a solution comprising a polymer and the compound of the present invention to yield a solvent swollen gel composition comprising the fluorinated aminoborate monoanion of the present invention. Alternatively, a monomer or a precursor of a polymer and the compound of the present invention can be mixed and subjected to a polymerization reaction to form a polymer which comprises the fluorinated aminoborate monoanion of the present invention. If the resulting polymer is a solid, an appropriate solvent can be added to provide a gelatinous form of the mixture. Polymerization conditions necessary for preparing such a polymer depends on the nature of the monomer or the precursor of the polymer, which are well known to one of ordinary skill in the art of polymerization.

A molten salt comprising a fluorinated aminoborate monoanion of the present invention can also be prepared by heating the compound of the present invention until it becomes a liquid. In this manner, a molten salt with high electric conductivity can be obtained. Moreover, it will be appreciated that the melting temperature of the compound of the present invention can be lowered by adding an additive. It is well known to one of ordinary skill in the art that a presence of an impurity lowers the melting point of most solids. Thus, a molten salt or a liquid comprising the compound of the present invention at a desired temperature can be prepared by selecting an appropriate impurity and an appropriate amount of the impurity.

Another embodiment of the present invention provides a method for producing fluorinated aminoborate monoanions of the present invention. The method generally includes contacting an aminohydroborate compound of the formula M[H$_3$N—B$_a$H$_{(a-1)}$]$_x$ with a mixture of HF (preferably anhydrous HF) and F$_2$ to produce a compound of the formula M[H$_3$N—B$_a$H$_b$F$_c$]$_x$, where M, a, b, c, and x are those defined above. As used herein "anhydrous HF" refers to HF having less than about 10% water, preferably less than about 2% water, and more preferably less than about 0.5% water.

Fluorination of an aminohydroborate compound generally involves cooling the reaction vessel containing the aminohydroborate compound of the formula M[H$_3$NB$_a$H$_{a-1}$]$_x$ to a temperature sufficient to allow condensation of anhydrous HF. Typically, the reaction vessel is cooled to about −78° C. Preferably from about 10 equivalents (equiv.) of HF to about 1000 equiv. of HF is added to the reaction vessel, more preferably from about 200 equiv. to about 700 equiv., and most preferably from about 300 equiv. to about 500 equiv.

In addition, methods of the present invention can also include adding F$_2$ to the reaction vessel. Fluorine gas can be added in a pure form or it can be added as a dilute gaseous solution. A dilute gaseous solution of fluorine can be formed by mixing fluorine gas with an inert carrier gas such as nitrogen, helium or argon. Preferably the carrier gas is nitrogen. For a small scale reaction, it is particularly preferred that the fluorine gas be added as a dilute gaseous solution, as this allow better control of the total amount of fluorine gas added to the reaction mixture. When fluorine gas is added as a dilute gaseous solution, the amount of fluorine gas present in the dilute gaseous solution is typically from about 50 mole % to about 0.1 mole % of the carrier gas, preferably from about 20 mole % to about 1 mole %, and more preferably from about 20 mole % to about 10 mole %.

Addition of fluorine gas to the reaction mixture typically involves cooling the reaction vessel to about −78° C. and addition of (e.g., by condensing) the desired amount of fluorine gas into the reaction vessel. Preferably from about 5 equiv. of fluorine to about 20 equiv. of fluorine is added to the reaction vessel, more preferably from about 10 equiv. to about 16 equiv., and most preferably from about 13 equiv. to about 15 equiv.

After the addition of necessary reactants, the reaction vessel, e.g., Monele reactor, is typically sealed to provide a closed system, and the reaction mixture is mixed by any appropriate method of providing agitation of the reaction mixture, for example, rotating or shaking the reaction vessel, or stirring the reaction mixture. Typically the reaction mixture is brought back to room temperature, or preferably to about 30° C., and the reaction vessel is rotated (i.e., spun) or shaken to provide a sufficient mixing of the reactants to allow a desired reactionto occur. It will be appreciated that when the reaction mixture is brought to room temperature or about 30° C., the pressure inside the reaction vessel will increase significantly due to because of the vapor pressure of fluorine and HF. Therefore, the reaction vessel should be carefully selected to be able to withstand this increase in pressure. Preferably the reaction time is from about 1 h to about 72 h, more preferably from about 5 h to about 48 h, and most preferably from about 8 h to about 24 h. The final reaction temperature is less than about 100° C., and more preferably less than about 50° C. Most preferably the final reaction temperature is at about 30° C. The compound of the formula $M[H_3N—B_aH_bF_c]_x$ thus produced can be isolated by removing any remaining gaseous reactant, e.g., HF, and/or fluorine.

Alternatively, fluorination of an aminohydroborate compound can be conducted in a continuous process in which a stream of hydrogen fluoride and fluorine gases are continuously introduced to the aminohydroborate compound.

The method can further include the steps of contacting a non-alkylated fluorinated borate compound of the formula $M[H_3N—B_aH_bF_c]_x$, with $R^1–X^1$ to produce a monoalkyl aminoborate compound of the formula $M[R^1H_2N—B_aH_bF_c]_x$, where $X^1$ is a leaving group, and $R^1$, a, b, c and x are those defined above. Moreover, the monoalkyl aminoborate can be further alkylated with $R^2–X^2$ to produce a dialkyl aminoborate of the formula $M[R^1R^2HN—B_aH_bF_c]_x$, where $R^2$ is defined above, and $X^2$ is a leaving group. Furthermore, the dialkyl aminoborate can be alkylated with $R^3–X^3$ to produce a trialkyl aminoborate of the formula $M[R^1R^2R^3N—B_aH_bF_c]_x$, where $R^3$ is defined above, and $X^3$ is a leaving group. It should be appreciated that each of the above described alkylation steps can be conducted sequentially (i.e., separately) to afford $R^1$, $R^2$, and $R^3$ groups which are different from each other, or the alkylation steps can be conducted in a such manner to afford an alkyl fluorinated aminoborate compound having two or more of the $R^1$, $R^2$, and $R^3$ groups that are identical. Thus, while the alkylations steps are written as separate steps, the scope of the present invention includes reaction processes where two or more of $R^1–X^1$, $R^2–X^2$ and $R^3–X^3$ reagents are identical, e.g., dialkylation or trialkylation of the fluorinated aminoborate anion by $R^1–X^1$ or $R^2–X^2$ compound. It should be appreciate that when non-alkylated fluorinated borate compound is alkylated, at least one of the $R^1$, $R^2$, and $R^3$ groups is not hydrogen.

The nitrogen group can be protected according to the techniques known in the art before each alkylation steps to reduce or prevent more than one alkylation by the alkylating agent. Furthermore, if any of the $R^1$ or $R^2$ substituent contain a reactive functionality, then the substituent group can be protected to prevent or reduce a reaction with the alkylating agent. A variety of protecting groups are known in the art, and can be employed. Examples of many of the possible groups can be found in *Protective Groups in Organic Synthesis*, 3rd edition, T. W. Greene and P. G. M. Wuts, John Wiley & Sons, New York, 1999, which is incorporated herein by reference in its entirety.

Another embodiment of the present invention provides a compound comprising the fluorinated aminoborate monoanion produced by the process of the above described methods.

The present inventor have found that compounds of the present invention are co-catalyst (or activator) of olefin polymerization catalyst. Thus, in one aspect, compounds comprising a fluorinated aminoborate monoanion of the present invention are used as activators in a transition metal catalyzed olefin polymerization. Useful olefin polymerization catalysts include organometallic single site olefin polymerization catalysts such as metallocenes. Other suitable polymerization catalysts are disclosed, for example, in U.S. Pat. No. 5,278,119, which is incorporated herein by reference in its entirety. Preferably, the olefin polymerization catalyst is selected from the group consisting of metallocenes. More preferably, the olefin polymerization catalyst is selected from the group consisting of zirconecene, titanocene, and halfnocene. And most preferably, the olefin polymerization catalyst is selected from the group consisting of $Cp_2ZrR_2$, where each R is independently alkyl, CO, NO, halide, imine or phosphine.

Generally, a polymer of a higher molecular weight is obtained at a lower polymerization temperature because of slower chain transfer reactions at a lower temperature. However, in polymerization at a temperature lower than the melting temperature of the polymer, the polymer that is formed deposits in the reaction vessel, which retards agitation and reduces the productivity. In a solution polymerization process, where the polymerization is conducted at a temperature higher than the melting point of the polymer, the above disadvantages are reduced or eliminate. Moreover, the higher temperature decreases the viscosity of the polymerization solution, thereby increasing the agitation efficiency, which facilitates removal of polymerization heat and control of the reaction to produce a homogeneous polymer. In high-temperature high-pressure polymerization, the larger difference between the temperature of polymerization and the temperature of the feed of raw materials increases polymerization of the olefin.

The catalyst system of the present invention can be prepared by mixing the olefm polymerization catalyst, and the fluorinated aminoborate compound of the present invention. Such mixture can be prepared as a solid mixture or as a solution in an inert solvent.

The amount of olefin polymerization catalyst used the catalyst system of the present invention typically ranges from about $10^{-8}$ equiv. to about $10^{-2}$ equiv. relative to the total monomer (i.e., olefin) used. Preferably, the catalyst is used in the amount from about $10^{-7}$ equiv. to about $10^{-3}$ equiv. And more preferably, the amount of catalyst used in olefin polymerization is from about $10^{-6}$ equiv. to about $10^{-4}$ equiv.

The amount of fluorinated aminoborate compound present in the catalyst system typically ranges from about 0.5 equiv. to about 10 equiv. of the olefin polymerization catalyst. Preferably, from about 0.5 equiv. to about 5 equiv., more preferably from about 0.8 equiv. to about 3 equiv., and most preferably from about 1 equiv. to about 2 equiv.

While the olefin polymerization catalyst system of the present invention does not require aluminoxane, it is possible and sometimes may be desirable to add an aluminoxane in addition to the fluorinated aminoborate compound of the present invention. When an aluminoxane is present in the olefin polymerization catalyst system, the amount of aluminoxane used ranges preferably from 10 to 500 equiv. relative to the olefin polymerization catalyst.

Any compound containing an olefin moiety (i.e., carbon-carbon double bond) can be polymerized by the catalyst system of the present invention. Exemplary olefins include ethylene; α-olefins, such as propylene, 1-butene, 4-methyl-1-pentene, 1-hexene, 1-octene, 1-decene, 1-dodecene, 1-tetradecene, 1-hexadecene, styrene, and p-methylstyrene; dienes such as butadiene, 1,5-hexadiene, 1,4-hexadiene, ethylidenenorbornene, and vinylidenenorbomene. However, it should be appreciated that olefin polymerization processes of the present invention is limited to those listed above. It should also be recognized that two or more olefins can be used in combination to produce co-polymers.

Olefin polymerization processes of the present invention include batch polymerization and continuous polymerization. In addition, olefin polymerization processes of the present invention include solution polymerization employing a solvent, and high-temperature high-pressure polymerization, which are well known to one of ordinary skill in the art.

In one aspect, the solution olefm polymerization can be conducted under the polymerization conditions as follows. The polymerization temperature is typically at least about 0° C. The higher temperature is considered to be advantageous in polymer productivity owing to lower solution viscosity and removal of polymerization heat. Therefore, the polymerization temperature ranges preferably from about 0° C. to about 200° C., more preferably from about 25° C. to about 180° C., more preferably from about 50° C. to about 150° C., and most preferably from about about 100° C. to about 150° C. At these polymerization temperature, the resulting polymers have a relatively high molecular weight. The polymerization pressure is generally in the range of from atmospheric pressure to about 500 kg/cm². However, other polymerization pressure can also be used.

The solution polymerization can be carried out in a variety of inert organic solvents. The type of solvent used depends on a variety of factors including the polymerization temperature, polymerization pressure, reactivity of the catalyst system as well as other factors. In general, however, suitable organic solvents include hydrocarbons such as unsaturated hydrocarbons (e.g., toluene, benzene, and xylenes), and saturated hydrocarbons (e.g., hexane and isooctane). Preferably, the polymerization solvent is selected from the group consisting of toluene and isooctane. And more preferably, the polymerization solvent is isooctane.

The present invention provides an olefin polymer having a high molecular weight, narrow molecular weight distribution, and narrow composition distribution by conducting polymerization of ethylene and/or an α-olefin by use of a constrained geometry catalyst of a specified structure at high temperature. The presence of a fluorinated aminoborate compound in the olefin catalyst system of the present invention results in a higher catalytic activity for olefin polymerization catalysts.

Compounds of the present invention can also be used as cocatalyst in copolymerization of olefins with carbon monoxide.

Additional objects, advantages, and novel features of this invention will become apparent to those skilled in the art upon examination of the following examples thereof, which are not intended to be limiting.

EXAMPLES

Example 1

This example illustrates a method for synthesizing an aminoborate of the formula $Cs(H_3NB_{12}H_{11})$.

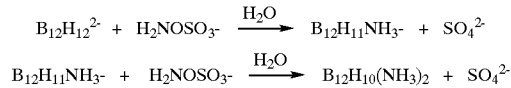

In a typical preparation, a solution of $K_2B_{12}H_{12}$ (3.29 g, 0.015 mol) and $NH_2OSO_3H$ (1.92 g, 0.017 mol) in 70 mL of water was refluxed for 2.5 h. The solution was cooled to room temperature and; was analyzed by $^{11}B$ NMR spectroscopy. Integration of the NMR resonances showed that approximately 50% of the unsubstituted $B_{12}H_{12}{}^{-2}$ starting material had not reacted under these conditions. The amounts of two amminoborate derivatives were determined by integration of $^{11}B$ NMR resonances from nitrogen-substituted boron atoms (B(N),δ $^{11}B$=−5 to −10) and resonances from hydrogen-substituted boron atoms (B(H),δ $^{11}_{B=-}$12 to −24). An additional amount of $H_2NSO_3H$ (1.1 g, 0.01 mol) was added to the solution, and the resulting mixture was refluxed for an additional 2 h. After this procedure the ratio of B(N) to B(H) atoms in the reaction mixture was 1:11.5, but the $^{11}B$ NMR resonance from $B_{12}H_{12}{}^{-2}$ was still present. These data indicate that di-ammonio derivatives (at least two isomers) were present in the solution; therefore, no additional $H_2NOSO_3H$ was added to the reaction mixture. It is important that no signals attributable to boric acid were observed; boric acid is a typical decomposition product of some borate clusters in aqueous solution. This indicates that no noticeable decomposition of $B_{12}H_{12}{}^{-2}$ occurred during the reaction and that the ammonio derivatives of this anion are the only boron-containing reaction products.

The volume of the reaction solution was reduced under vacuum to about 15 mnL. The concentrated solution was treated with a solution of CsCl (3.5 g, 0.026 mol) in 5 mL of water. After cooling to 0° C., a white precipitate (mixture of compounds) was collected by filtration and washed with a small amount of cold water. The solid was dried, and recrystallized from 450 mL of acetonitrile. The solubility of $Cs_2B_{12}H_{12}$ in $CH_3CN$ is negligible while the solubility of $CsB_{12}H_{11}NH_3$ in $CH_3CN$ was found to be approximately 0.3 g/100 mL. The acetonitrile-insoluble fraction (2.0 g) was greater than 90% $Cs_2B_{12}H_{12}$ with small amounts of the other derivatives. The acetonitrile-soluble fraction contained $Cs(H_3NB_{12}H_{11})$ and what appears to be isomeric mixtures of $CsB_{12}H_{10}(NH_2)(NH_3)$ derivatives. In the final stage of the purification process, acetonitrile was removed under vacuum and the residue was washed twice with 5 mL of acetonitrile to remove the $CsB_{12}H_{10}(NH_2)(NH_3)$ derivatives. The solid residue that remained, $Cs(H_3NB_{12}H_{11})$, was dried under vacuum (yield 1.40 g, 32% based on $Cs_2B_{12}H_{12}$). The purity of $Cs(H_3NB_{12}H_{11})$ was confirmed by negative ion electrospray mass spectrum (NIEMS) and by $^{11}B$ and $^{1}H$ NMR spectra. From the aqueous filtrate and $CH_3CN$ washes, 0.8 g of additional (tan) solid was isolated and was characterized as a mixture of $CsB_{12}H_{10}(NH_2)(NH_3)$ (~80 mol %) and $Cs(H_3NB_{12}H_{11})$ (~20 mol %). The $^{1}H\{^{11}B\}$ NMR spectrum suggest the formation of both the 1,2 and 1,7 isomers of $CsB_{12}H_{10}(NH_2)(NH_3)$.

Example 2

This example illustrates a result of a reaction between $Cs(H_3NB_{12}H_{11})$ and liquid anhydrous hydrogen fluoride (LAHF).

The compound $Cs(H_3NB_{12}H_{11})$ (0.30 g, 1.03 numol) was treated with 20 mL of LAHF for 2 days in a 30-mL Teflon reactor. All volatiles were removed under vacuum and 0.28 g of white solid was collected. Boron-11 NMR spectra of this solid showed that the $H_3NB_{12}H_{11}^-$ anion was recovered almost quantitatively (only very low intensity peaks were observed in the $^{19}F$ NMR spectrum of the reaction mixture).

Example 3

This example illustrates a method for synthesizing a compound comprising fluorinated aminoborate of the formula: $H_3NB_{12}F_{11}^-$.

In a typical preparation, a mixture of $Cs(H_3NB_{12}H_{11})$ (0.65 g, 2.24 mmol) and LAHF (60 mL) was treated with elemental fluorine (29.16 mmol, 13 equiv.) in a 300 mL Monel reactor (60, 60 and 24 psia of a 20% $F_2/N_2$ mixture were added after the reaction mixture had been cooled to −78° C. and evacuated; the reactor was rotated for from about 20 h to about 24 h at about 30° C. after each addition). All volatiles were then removed under vacuum, and a gray solid was isolated under a nitrogen atmosphere in a glove box. Boron-11 and $^{11}F$ NMR spectra of the solid indicated the presence of two anions, $BF_4^-$ (about 68 mol %) and $H_3NB_{12}F_{11}^-$ (about 32 mol %). There were also trace amounts of other species. Assuming that all boron-containing species were derived from $H_3NB_{12}H_{11}^-$, the conversion of $H_3NB_{12}H_{11}^-$ to the desired product $H_3NB_{12}F_{11}^-$ can be estimated as about 81% (with about 19% $B_{12}$ cluster decomposition to $BF_4^-$; this assumes that all clusters that decompose form 12 $BF_4^-$ anions). Without being bound by any theory, a proposed reaction, without decomposition products, is shown below.

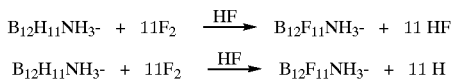

In another experiment, $Cs(H_3NB_{12}F_{11})^-$ (0.30 g, 1.03 mmol) was treated with only 5.7 equiv. $F_2$ (5.84 mmol) in LAHF. Boron-11 and $^{11}F$ NMR spectra of the crude reaction product, after LAHF had been removed under vacuum, indicated that a mixture of only three anions was present: $BF_4^-$ (about 8 mol %); $H_3NB_{12}F_{11}^-$ (about 68 mol %); and unreacted $H_3NB_{12}H_{11}^-$ (about 24 mol %). In this reaction, the amount of the decomposition product $BF_4^-$ was much smaller than in the reaction with 13 equiv. $F_2$. Theoretically, for every $H_3NB_{12}H_{11}^-$ cluster that was decomposed into 12 $BF_4^-$ anions during the reaction, 94 $H_3NB_{12}H_{11}^-$ clusters were transformed into undecafluoro $H_3NB_{12}F_{11}^-$ anions.

The compound $[N(n-Bu)_4][H_3NB_{12}F_{11}]$ contaminated with about 24 mol % of $[N(n-Bu)_4][BF_4]$ can be isolated in the following way. The solid product mixture from the reaction of 0.3 g of $CsB_{12}H_{11}NH_3$ with 12 equiv. of fluorine in LAHF was dissolved in 50 mL of water and the insoluble material was removed by filtration. Addition of $[N(n-Bu)_4]Cl$ to the filtrate caused the formation of 145 mg of a white precipitate ($[N(n-Bu)_4][H_3NB_{12}F_{11}]$ contaminated with $[N(n-Bu)_4][BF_4]$).

Example 4

This example illustrates a method for synthesizing a compound comprising fluorinated aminoborates of the formula: $Me_3NB_{12}F_{11}^-$, $EtH_2NB_{12}F_{11}^-$ and $Et_2HNB_{12}F_{11}^-$.

The alkylation reaction for R=Me is shown below:

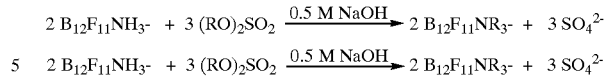

In a typical experiment, a mixture of $Cs(H_3NB_{12}H_{11})$ (0.58 g, 2.00 mmol) and LAHF (60 mL) was treated with 24.3 mmol $F_2$ (12 equiv.) for 48 h. All volatiles were removed under vacuum and 0.82 g of a gray solid were collected. The solid was dissolved in 40 mL of 0.5 M aqueous NaOH and a blue-green precipitate that formed was removed by filtration. When the blue-green precipitate was redissolved in 1 M HCl and a $^{11}B$ NMR spectrum recorded, the presence of only trace amounts of $BF_4^-$ or other boron-containing species were observed. Without being bound by any theory, it is believed that the blue-green precipitate was $Ni(OH)_2$, $Cu(OH)_2$, or a mixture of these two compounds, where the nickel and/or copper are believed to be derived from the walls of the Monel reactor. The filtrate was treated with 1 mL of $(CH_3O)_2SO_2$ for 1 hour, during which time a white precipitate was formed. Ethanol (about 1 mL) was added to the mixture. The resulting mixture was neutralized with conc. HCl to about pH 1, and the white solid was collected by filtration, and dried under vacuum to yield 135 mg of $[Me_4N][Me_3NB_{12}F_{11}]$ (16% based on $Cs(H_3NB_{12}H_{11})$). Without being bound by any theory, it is believed that the formation of the $NMe_4^+$ cation is probably due to the presence of $[NH_4][BF_4]$ in the crude fluorination reaction mixture.

The filtrate having about pH 1 was then treated with 1 mL conc. HCl and extracted from the aqueous phase with two 50 mL portions of diethyl ether. The ether was then removed under vacuum. The resulting oily residue was dissolved in 5 mL of water, and 2 mL of an aqueous solution of CsCl was added. The white precipitate that formed was collected by filtration, washed with cold water, and dried under vacuum to yield 0.11 g of $Cs(Me_3NB_{12}F_{11})$ (11% yield).

An NMR analysis of the aqueous phase after the ether extraction showed the presence of polyhedral borate anions. The addition of $[N(n-Bu)_4]Cl$ to this fraction afforded the isolation of solid $[N(n-Bu)_4][Me_3NB_{12}F_{11}]$ (0.150 g, 13% yield, about 90% pure). In a separate experiment it was shown that fluorinated amino derivative of polyhedral borate anions can be substantially completely extracted from the acidic aqueous solution into a larger amount of diethyl ether. The total yield of $Me_3NB_{12}F_{11}^-$ from $H_3NB_{12}H_{11}^-$ was ~40%.

When $(EtO)_2SO_2$ was used as the alkylating agent instead of $(MeO)_2SO_2$, the formation of $Et_{(3-n)}H_nNB_{12}F_{11}^-$ anions was observed (where n=1 or 2). The addition of $PPh_4Cl$ to the reaction mixture afforded the isolation of solid $[PPh_4][Et_{(3-n)}H_nNB_{12}F_{11}]$.

Example 5

This example illustrates a method for producing $Li(Me_3NB_{12}F_{11})$.

In a typical preparation, the compound $[NMe_4][Me_3NB_{12}F_{11}]$ (0.135 g) was dissolved in 100 mL of methanol. The solution was passed through a column packed with XN-1010® cation exchange resin in its acidic forn. The eluent was slightly yellow. Methanol was removed under vacuum and the oily residue was dissolved in 2 mL water. A small amount of the solid did not dissolve and was removed by filtration. The filtrate was neutralized with LiOH to about pH 7 and water was removed under vacuum, leaving a tan solid. The solid was dried under vacuum at 190° C. for 24 h and was characterized by $^{11}$B, $^{19}$F, $^1$H NMR and by NIEMS as pure, anhydrous Li(Me$_3$NB$_{12}$F$_{11}$).

Example 6

This example illustrates a method for synthesizing [CPh$_3$][Me$_3$NB$_{12}$F$_{11}$].

A mixture of Li(Me$_3$NB$_{12}$F$_{11}$) (35 mg, 0.09 mmol) and CPh$_3$Cl (24 mg, 0.09 mmol) was stirred in 2 mL dichloromethane for about 24 h. The insoluble material was removed by filtration in a nitrogen-filled glove box and dichloromethane was removed under vacuum. The yellow solid was washed three times with 1 mL isooctane and was dried under vacuum. The solid was redissolved in 1 mL dichloromethane and was characterized by $^{19}$F and $^1$H NMR spectroscopy as [CPh$_3$][Me$_3$NB$_{12}$F$_{11}$]. The x-ray crystal structure of this compound is shown in FIG. 1. The compound [CPh$_3$][Me$_3$NB$_{12}$F$_{11}$] has a low solubility and is stable for days in dichloromethane but is insoluble in toluene.

Example 7

This example illustrates alkylation of H$_3$NB$_{12}$F$_{11}^-$ with RBr (R=Bu, Bn, Hx, Oc, an Dd, i.e., butyl, benzyl, hexyl, octyl and dodecyl, respectively).

Treatment of Cs(H$_3$NB$_{12}$F$_{11}$) with BuBr (i.e., butyl bromide) for 2 h at 90° C. in 0.5 M aqueous NaOH produced BuHNB$_{12}$F$_{11}^{-2}$ (70%) along with the deprotonated starting material, H$_2$NB$_{12}$F$_{11}^{-2}$ (30%). Refluxing the reaction mixture for 15 h afforded a mixture of BuHNB$_{12}$F$_{11}^{-2}$ (30%) and Bu$_2$NB$_{12}$F$_{11}^{-2}$ (70%); a small amount of the completely alkylated Bu$_3$NB$_{12}$F$_{11}^-$ anion was observed in a negative-ion electrospray mass spectrum (NIEMS) of the reaction mixture. Methylation of BuHNB$_{12}$F$_{11}^{-2}$ and Bu$_2$NB$_{12}$F$_{11}^{-2}$ with SO$_2$(OMe)$_2$, to afford BuMe$_2$NB$_{11}$F$_{11}^-$ and Bu$_2$MeNB$_{11}$F$_{11}^-$, respectively.

Refluxing a 0.5 M NaOH solution of Cs(H$_3$NB$_{12}$F$_{11}$), OcBr (octylbromide), and TBA$^+$Cl$^-$ (i.e., tetrabutylammonium chloride) for 48 h led to the formation of the completely alkylated anion Oc$_3$NB$_{12}$F$_{11}^-$ contaminated with only a small amount of Oc$_2$NB$_{12}$F$_{11}^{-2}$. Similar conditions were used to prepare the Hx$_3$NB$_{12}$F$_{11}^{-1}$ and Dd$_3$NB$_{12}$F$_{11}^{-1}$ anions.

Treatment of Cs(H$_3$NB$_{12}$F$_{11}$) with BnBr (i.e., benzyl bromide) in THF in the presence of TBA$^+$F$^-$ for 2 days at 25° C. led to the formation of a small amount of Bn$_2$HNB$_{12}$F$_{11}^{-1}$. Other compounds present include the starting material, H$_3$NB$_{12}$F$_{11}^{-1}$, as well as BnH$_2$NB$_{12}$F$_{11}^{-1}$. When BuBr was used as the alkylating reagent and KF was used as the base instead of TBA$^+$F$^-$, no reaction was observed at 25° C. However, when this reaction mixture was refluxed for 6 days, the formation of Bu$_2$HNB$_{12}$F$_{11}^{-2}$ was observed. The product required additional purification. When NaH and CaH$_2$ were tested as bases for these alkylation reactions, only low conversions to alkylated products were observed.

Example 8

This example illustrates a synthesis of [CPh$_3$][Bu$_2$MeNCB$_{11}$F$_{11}$] and Li(Bu$_2$MeNB$_{12}$F$_{11}$).

A mixture of Cs(H$_3$NB$_{12}$H$_{11}$) (0.79 g, 2.72 mmol) and anhydrous HF (45 mL) was treated with F$_2$ (24.8 mmol, 9 equiv.) for 48 h. Volatiles were removed under vacuum, leaving 0.89 g of a gray solid. According to $^{11}$B and $^{19}$F NMR spectra of the solid, it consisted of a mixture of salts of three anions, the desired product, H$_2$NB$_{12}$F$_{11}^{-2}$, the starting material, H$_3$NB$_{12}$H$_{11}^{-1}$, and BF$_4^{-1}$, a decomposition product. The overall yield of Cs(Bu$_2$MeNB$_{12}$F$_{11}$) was about 34%.

The crude gray solid (0.57 g) was dissolved in 0.5 M aqueous NaOH (50 mL). The blue-green precipitate that formed was removed by filtration. The filtrate was treated with BuBr (1.5 mL) for 15 h at 95° C. A $^{19}$F NMR spectrum of the solution indicated that nearly all of the H$_3$NB$_{12}$F$_{11}^{-1}$ ion originally present was converted to a mixture of BuHNB$_{12}$F$_{11}^{-2}$ (30 mol %) and Bu$_2$NB$_{12}$F$_{11}^{-2}$ (70 mol %). Heating the mixture for an additional 21 h resulted in an increase in the relative concentration of Bu$_2$NB$_{12}$F$_{11}^{-2}$ to about 83 mol %. The mixture was treated with an additional amount of BuBr (1 mL) for 7 hours at 95° C. and filtered. The $^{19}$F NMR spectrum of the filtrate indicated that the concentration ratio of [BuHNB$_{12}$F$_{11}^{-2}$] to [Bu$_2$NB$_{12}$F$_{11}^{-2}$] was about 5:95. The solution was then treated with dimethyl sulfate (2 mL) for 18 h, which caused the gradual formation of a white precipitate. The precipitate was separated by filtration, washed with cold water, and dried under vacuum. The yield of Cs(Bu$_2$MeNB$_{12}$F$_{11}$), which was contaminated with about 5% of Cs(BuMe$_2$NB$_{12}$F$_{11}$), was 0.36 g (34% based on Cs(H$_3$NB$_{12}$H$_{11}$)).

The compound Cs(Bu$_2$MeNB$_{12}$F$_{11}$) (0.300 g) was dissolved in 30 mL of methanol. The solution was eluted with methanol through a column packed with Rohm & Haas XN-1010 cation exchange resin in its acidic form. The eluent was slightly yellow. Methanol was removed under vacuum and the oily residue was dissolved in 10 mL water. The solution was neutralized with LiOH to about pH 7 and water was removed under vacuum, leaving a tan oily residue. The residue was dried under vacuum at 180° C. for 22 h. The yield of Li(Bu$_2$MeNB$_{12}$F$_{11}$) was 0.191 g (80% based on Cs(Bu$_2$MeNB$_{12}$F$_{11}$)).

A mixture of Li(Bu$_2$MeNB$_{12}$F$_{11}$) (0.180 g, 0.37 mmol) and CPh$_3$Cl (0.104 g, 0.37 mmol) was stirred in dichloromethane (30 mL) for 15 h. The insoluble material was removed by filtration under a nitrogen atmosphere and dichloromethane was removed under vacuum. The orange-yellow solid was washed three times with isooctane (3×10 mL) and was dried under vacuum. The solid CPh$_3$(Bu$_2$MeNB$_{12}$F$_{11}$) still contained about 13 mol % of CPh$_3$Cl (determined by quantitative $^1$H NMR spectroscopy). The solid was recrystallized from toluene and dichloromethane. The yield of CPh$_3$(Bu$_2$MeNB$_{12}$F$_{11}$) was 0.150 g. The compound CPh$_3$(Bu$_2$MeNB$_{12}$F$_{11}$) has a high solubility in dichloromethane and is sparingly soluble in benzene and toluene. In contrast, CPh$_3$(Me$_3$NB$_{12}$F$_{11}$,) has a low solubility in dichloromethane and is insoluble in aromatic hydrocarbon solvents.

Example 9

This example illustrates a method for purifying a compound containing H$_2$NB$_{12}$F$_{11}^{-2}$ dianion.

The present inventors have found that H$_3$NB$_{12}$F$_{11}^{-1}$ can be partially separated from BF$_4^{-1}$ by fractional crystallization of their NBu$_4^{+1}$ salts from water, because [NBu$_4$][BF$_4$] has a higher solubility in water than [NBu$_4$][H$_3$NB$_{12}$F$_{11}$]. Furthermore, the present inventors have discovered that addition of NBu$_4$Cl to an 0.5 M aqueous KOH solution containing BF$_4^{-1}$ and H$_2$NB$_{12}$F$_{11}^{-2}$ results in the precipitation of pure [NBu$_4$]$_2$[H$_2$NB$_{12}$F$_{11}$].

In a typical experiment, the crude solid product from the fluorination of Cs(H$_3$NB$_{12}$F$_{11}$) (1.00 g) was dissolved in water (100 mL) and treated with 10 mL of 5 M aqueous KOH. The mixture was stirred for 1 h and a blue-green precipitate was removed by filtration. The filtrate was treated with an aqueous solution of NBu$_4$Cl, and the white precipitate that formed was collected by filtration, washed with water and dried under vacuum. According to $^{11}$B and $^{19}$F NMR spectra, the isolated compound was a substantially pure [NBu$_4$]$_2$[H$_2$NB$_{12}$F$_{11}$] compound (1.12 g, 41% based on Cs(H$_3$NB$_{12}$H$_{11}$)).

Example 10

This example illustrates effects of phase transfer catalyst on alkylation of a compound containing H$_3$NB$_{12}$F$_{11}^{-1}$ monoanion.

As shown above, a compound containing H$_3$NB$_{12}$F$_{11}^{-1}$ monoanion reacts with RBr (R=Hx, Oc, Dd) in 0.5 M aqueous KOH solution at 100° C. in the presence of the phase transfer cation TBA$^{+1}$. Effective alkylations occurred when the ratio of TBA$^+$Br$^{-1}$ to Cs(H$_3$NB$_{12}$F$_{11}$) was $\geq$1 or when [TBA][H$_3$NB$_{12}$F$_{11}$] was used as the starting material for the alkylation reaction. When a catalytic amount of TBA$^+$Br$^-$ was used, the N-alkylations proceeded slowly or were incomplete. For example, when Cs(H$_3$NB$_{12}$F$_{11}$) was refluxed in 0.5 M aqueous KOH with an excess of DdBr in the presence of only 0.1 equiv. TBA$^+$Br$^-$, significant amounts of unreacted H$_3$NB$_{12}$F$_{11}^{-1}$ were still present in the reaction mixture after 22 h. However, when equal molar amounts of Cs(H$_3$NB$_{12}$F$_{11}$) and TBA$^+$Br$^-$ were used, H$_3$NB$_{12}$F$_{11}^{-1}$ was not observed in the reaction mixture after the same period of time. The reaction products were salts of Dd$_2$NB$_{12}$F$_{11}^{-2}$ and Dd$_3$NB$_{12}$F$_{11}^{-1}$.

Refluxing CH$_3$CN solutions of Cs(H$_3$NB$_{12}$F$_{11}$) with RBr in the presence of K$_2$CO$_3$ and catalytic amounts of the cyclic polyether 18-crown-6 resulted in a lower degree of alkylation than refluxing 0.5 M NaOH solutions of Cs(H$_3$NB$_{12}$F$_{11}$) with RBr. For example, refluxing a CH$_3$CN solution of Cs(H$_3$NB$_{12}$F$_{11}$) and HxBr in the presence of 5 equiv. of K$_2$CO$_3$ and 0.1 equiv. of 18-crown-6 ether for 48 h led to the formation of mostly dialkylated Hx$_2$NB$_{12}$F$_{11}^{-2}$ with only traces of trialkylated Hx$_3$NB$_{12}$F$_{11}^{-1}$. On the other hand, refluxing a 0.5 M NaOH solution of Cs(H$_3$NB$_{12}$F$_{11}$), HxBr, and TBA$^+$Cl$^-$ for 48 h led to the formation of mostly trialkylated Hx$_3$NB$_{12}$F$_{11}^{-1}$.

Example 11

This example illustrates the effect of steric size of the alkylating agent on alkylation of a compound containing H$_3$NB$_{12}$F$_{11}^{-1}$ monoanion.

The rate and degree of N-alkylation of H$_3$NB$_{12}$F$_{11}^{-1}$ dependent on the size of the alkyl group. When HxBr, OcBr, and DdBr were used as alkylating reagents with TBA (H$_3$NB$_{12}$F$_{11}$) in refluxing 0.5 M KOH (1 h reaction time), the dialkylated anions R$_2$NB$_{12}$F$_{11}^{-1}$ were the major reaction products (from about 80 mol % to about 90 mol %). Subsequent methylation of R$_2$NB$_{12}$F$_{11}^{-1}$ with (MeO)$_2$SO$_2$ to afford R$_2$MeNB$_{12}$F$_{11}^{-1}$ occurred within 1 h at 24° C. However, trialkylations of H$_3$NB$_{12}$F$_{11}^{-1}$, to afford R$_3$NB$_{12}$F$_{11}^{-1}$, were complete only after refluxing for 48 h in the presence of excess of RBr. When C$_6$H$_5$CH$_2$Br or C$_6$H$_{11}$CH$_2$Br (i.e., Mc-Br) were used as alkylating reagents, only dialkylated derivatives R$_2$NB$_{12}$F$_{11}^{-2}$ were observed in the reaction mixtures, even after refluxing for 48 h. Thus, the use of bulky alkyl groups provides a good way to synthesize pure dialkylated anions R$_2$HNB$_{12}$F$_{11}^{-1}$.

Example 12

This example illustrates a method for synthesizing a variety of salts containing a R$_x$H$_{(3-x)}$NB$_{12}$F$_{11}^{-1}$ monoanion.

The work-up of the alkylation reaction mixtures led to the isolation of [TBA][R$_x$H$_{(3-x)}$NB$_{12}$F$_{11}$] salts. For example, the compounds [TBA][R$_3$NB$_{12}$F$_{11}$] (R=Hx, Oc, Dd) were extracted from alkylation reaction mixtures with benzene or with a large excess of RBr. Benzene and any other volatile organic compounds were removed by vacuum distillation at elevated temperature, leaving an oily residue of [TBA][R$_3$NB$_{12}$F$_{11}$]. The compounds [TBA]$_2$[R$_2$NB$_{12}$F$_{11}$] (R=Bn, Mc) were not soluble in benzene and were separated by filtration. Ion-exchange chromatography (Rohm & Haas XN-1010 cation exchange resin; MeOH eluent) afforded [H(MeOH)$_x$][R$_x$H$_{(3-x)}$NB$_{12}$F$_{11}$] from [TBA][R$_x$H$_{(3-x)}$NB$_{12}$F$_{11}$]. Neutralization of these acid salts with LiOH, CsOH, or NBu$_3$ led to the formation of Li$^{+1}$, Cs$^{+1}$, or NBu$_3$H$^{+1}$ salts of R$_x$H$_{(3-x)}$NB$_{12}$F$_{11}^{-1}$. Compound of the formula [TBA][R$_3$NB$_{12}$F$_{11}$], where R=Hx, Oc, or Dd, are highly soluble in aromatic hydrocarbon solvents. It should be also noted that many TBA$^{+1}$ salts, including salt containing Cl$^{-1}$, BF$_4^{-1}$, and PF$^{6-}$, are insoluble or very sparingly soluble in aromatic solvents.

Cesium salts of R$_x$H$_{(3-x)}$NB$_{12}$F$_{11}^{-1}$ may be isolated directly from the alkylation reaction mixtures if TBA$^{+1}$ was not used as a phase transfer cation. However, the present inventors have found that the separation of [TBA][Dd$_3$NB$_{12}$F$_{11}$] from the organic constituents of the reaction mixture, including 1-DdBr and 1-DdOH, is much easier than the separation of Cs(Dd$_3$NB$_{12}$F$_{11}$) or Li(Dd$_3$NB$_{12}$F$_{11}$) from these organic compounds. It is believed that this is due to the (unexpected and highly significant) fact that Cs(Dd$_3$NB$_{12}$F$_{11}$) and Li(Dd$_3$NB$_{12}$F$_{11}$) are very soluble in aliphatic hydrocarbons but [TBA][Dd$_3$NB$_{12}$F$_{11}$] is not. Therefore, the pure salt [TBA][Dd$_3$NB$_{12}$F$_{11}$] can be obtained by washing with hexane and drying at 120° C. under vacuum.

Example 13

This example illustrates two different methods for synthesizing [CPh$_3$][R$_3$NB$_{12}$F$_{11}$].

In the first method, Li$^{+1}$ or Ag$^{+1}$ salts of R$_3$NB$_{12}$F$_{11}^{-1}$ were treated with CPh$_3$Cl in DCM (i.e., dichloromethane). The insoluble byproducts were removed by filtration and [CPh$_3$][R$_3$NB$_{12}$F$_{11}$] was isolated from the filtrate. Use of Cs(R$_3$NB$_{12}$F$_{11}$) instead of Li$^{+1}$ or Ag$^{+1}$ salts did not cause formation of [CPh$_3$][R$_3$NB$_{12}$F$_{11}$]. It is believed that this is due to the lower electrophilicity of Cs$^{+1}$ relative to Li$^{+1}$ or Ag$^{+1}$.

In the second method, Cs(Dd$_3$NB$_{12}$F$_{11}$) was converted to [CPh$_3$][R$_3$NB$_{12}$F$_{11}$] in one step by a metathesis reaction with CPh$_3$BF$_4$. In a typical reaction, a mixture of Cs(Dd$_3$NB$_{12}$F$_{11}$) and CPh$_3$BF$_4$ was stirred in DCM for several hours. The insoluble byproduct was removed by filtration and [CPh$_3$][Dd$_3$NB$_{12}$F$_{11}$] was isolated from the yellow filtrate as a yellow-brown sticky solid. The compound [CPh$_3$][Dd$_3$NB$_{12}$F$_{11}$] is highly soluble in DCM and TOL (i.e., toluene) and is sparingly soluble in isooctane. It was found that the purity of the Li$^{+1}$, Cs$^{+1}$ or Ag$^{+1}$ salts of R$_3$NB$_{12}$F$_{11}^{-1}$ is one of the important factor in the preparation of [CPh$_3$][Dd$_3$NB$_{12}$F$_{11}$].

It was found that [CPh$_3$][Dd$_3$NB$_{12}$F$_{11}$] is stable in anhydrous DCM under a nitrogen atmosphere for at least 1 week. It was also stable (i.e., no change in its $^1$H NMR) in the solid state under a nitrogen atmosphere for at least 3 months. Even more significantly, less than about 30% of the compound [CPh$_3$][Dd$_3$NB$_{12}$F$_{11}$] had decomposed after 3 months storage in the air.

Example 14

This example illustrates a method for synthesizing Cs(Hx$_3$NB$_{12}$F$_{11}$).

A mixture of $Cs(H_3NB_{12}H_{11})$ (0.50 g, 1.72 mmol) and anhydrous HF (45 mL) was treated with 20% $F_2/N_2$ (20.6 mmol F2, 12 equiv.) for 48 h. Volatiles were removed under vacuum, leaving 0.71 g of a gray solid. The gray solid (0.60 g) was dissolved in 0.5 M aqueous KOH (70 mL). The blue-green precipitate that formed was removed by filtration. The filtrate was treated with HxBr (3 nmL) and $NBu_4Br$ for 18 h at 90° C. The mixture was treated with an additional amount of HxBr (3 mL) for 30 h at 90 ° C. The $^{19}F$ NMR spectrum of the organic fraction of the mixture indicated that substantially all of the $H_3NB_{12}F_{11}^{-1}$ ion originally present in the aqueous fraction was converted to a mixture of $Hx_3NB_{12}F_{11}^{-2}$ (about 90 mol %) and $Hx_2NB_{12}F_{11}^{-2}$ (about 10 mol %). Substantially all of the anions were observed only in the organic fraction. The mixture was then treated with dimethyl sulfate (0.1 mL) for 3 h and extracted with benzene (50 mL). Benzene and other volatile organic compounds were removed by vacuum distillation at 60° C., leaving a light-yellow oil. The oil was heated under vacuum at 100° C. to remove other impurities. The sticky solid was dissolved in 100 mL of methanol. This solution was eluted with methanol through a column packed with Rohm & Haas XN-1010 cation exchange resin in its acidic form. The solution was neutralized with CsOH to about pH 7 and methanol was removed under vacuum, leaving an oily residue. The residue was dried under vacuum at 120° C. for 20 h, leaving a light-yellow glassy solid. The $^1H$ and $^{19}F$ NMR spectra of the solid indicated that it was a mixture of $Cs(Hx_3NB_{12}F_{11})$ (about 90 mol %) and $Cs(Hx_2MeNB_{12}F_{11})$ (about 10 mol %). The combined yield of both products was 0.34 g (27% based on $Cs(H_3NB_{12}H_{11})$).

Example 15

This example provides a method for producing $[Ag(C_6H_6)][Hx_3NB_{12}F_{11}]$.

A mixture of $Cs(Hx_3NB_{12}F_{11})$ (0.280 g, 0.378 nmmol) and $AgBF_4$ (0.075 g, 0.385 mmol) was stirred in BEN (i.e., benzene) for 3 h. The insoluble material was removed by filtration and BEN was removed under vacuum. The sticky solid was dried under vacuum at 24° C. for 1 day. According to $^1H$ NMR spectrum, the isolated compound was $[Ag(BEN)][Hx_3NB_{12}F_{11}]$. The compound was dried under vacuum at 80° C. for 24 h and a light-yellow glassy solid was collected. According to $^1H$ NMR spectrum, the isolated compound was $[Ag(BEN)_{0.5}][Hx_3NB_{12}F_{11}]$ (0.231 g, 81% yield).

Example 16

This example illustrates a method for synthesizing $[CPh_3][Hx_3NB_{12}F_{11}]$.

A mixture of $[Ag(BEN)_{0.5}][Hx_3NB_{12}F_{11}]$ (0.145 g, 0.192 mmol) and $CPh_3Cl$ (0.053 g, 0.19 mol) was stirred in DCM (10 mL) at 25° C. The reaction mixture rapidly became yellow and a white precipitate formed. After 1 h, the reaction mixture was filtered and DCM was removed from the filtrate under vacuum, leaving a yellow-orange sticky solid. The solid was dried under vacuum for 18 h and was washed with 30 mL of ISO (i.e., isooctane) followed by 30 mL of pentane, which removed the last traces of excess CTM (i.e., chlorotriphenylmethane). The yield of $[CPh_3][Hx_3NB_{12}F_{11}]$ was 0.124 g (76% based on $[Ag(BEN)_{0.5}][Hx_3NB_{12}F_{11}]$).

Example 17

This example illustrates a method for synthesizing $Cs(Dd_3NB_{12}F_{11})$.

A 1:1 mixture of $[NBu_4][H_3NB_{12}F_{11}]$ and $[NBu_4][BF_4]$ (1.10 g) was refluxed with DdBr (3 mL) in 0.5 M aqueous KOH for 18 h. The mixture was then refluxed with an additional amount of DdBr (3 mL) for 24 h. The compound $[NBu_4][Dd_3NB_{12}F_{11}]$ was extracted with benzene (50 mL). Benzene and other volatile organic compounds were removed by vacuum distillation at 120° C., leaving a light-yellow oil. The oil was washed two times with hexane (2×20 mL) and was dried at 120° C. for 18 h. The sticky solid was dissolved in methanol (100 mL). The solution was eluted with methanol through a column packed with Robin & Haas XN-1010 cation exchange resin in its acidic form. The solution was neutralized with CsOH to about pH 7 and filtered. Methanol was removed from the filtrate under vacuum, leaving an oily residue. The residue was dissolved in hexane (50 mL) and insoluble material (~0.020 g) was removed by filtration. Hexane was removed under vacuum and the oily residue was dried under vacuum at 140° C. for 16 h, leaving a light-yellow glassy solid. The yield of $Cs(Dd_3NB_{12}F_{11})$ was 0.81 g (57% based on $[NBu_4][H_3NB_{12}F_{11}]$).

The $^{19}F$ NMR resonances of $Cs(Dd_3NB_{12}F_{11})$ are shielded in lower dielectric solvents. Relevant data are listed in Table 1.

TABLE 1

NMR Data[a]

| compound | solvent | δ ($^{11}B$) (int.) | δ ($^{19}F$) (int.) | δ ($^1H$) (int.) |
|---|---|---|---|---|
| $[N(n-Bu)_4][H_3NB_{12}F_{11}]$ | ACN-$d_3$ | −14.1 (1) | −262.6 (1) | |
| | | −16.3 (10) | −263.7 (5) | |
| | | −33.3 (1) | −270.2 (5) | |
| $[N(n-Bu)_4][H_2NB_{12}F_{11}]$ | ACN-$d_3$ | −14.7 (1) | −265.2 (5) | |
| | | −16.4 (10) | −267.9 (5) | |
| | | −26.3 (1) | −268.5 (5) | |
| $[N(n-Bu)_4][(McH)_2HNB_{12}F_{11}]$ | ACN-$d_3$ | −13.4 (1) | −260.3 (1) | 4.67 (1) |
| | | −16.3 (10) | −263.3 (5) | 3.37 (4) |
| | | −29.3 (1) | −265.4 (5) | 1.70 (8) |
| | | | | 1.25 (8) |
| | | | | 1.03 (4) |
| $Cs[Me_3NB_{12}F_{11}]$ | ACN-$d_3$ | −13.4 (1) | −260.0 (1) | 3.15 (9) |
| | | −16.3 (10) | −263.5 (5) | |
| | | −28.1 (1) | −263.8 (5) | |
| $Cs[Hx_3NB_{12}F_{11}]$ | ACN-$d_3$ | −13.4 (1) | −258.8 (5) | 3.37 (6) |
| | | −16.2 (10) | −259.1 (1) | 1.76 (6) |

TABLE 1-continued

NMR Data[a]

| compound | solvent | δ ($^{11}$B) (int.) | δ ($^{19}$F) (int.) | δ ($^{1}$H) (int.) |
|---|---|---|---|---|
| | | −27.7 (1) | −262.5 (5) | 1.32 (18) |
| | | | | 0.90 (9) |
| Cs[Hx$_2$MeNB$_{12}$F$_{11}$] | ACN-d$_3$ | −13.4 (1) | −259.4 (1) | 3.30 (4) |
| | | −16.2 (10) | −260.4 (5) | 1.76 (3) |
| | | −27.7 (1) | −262.9 (5) | 1.32 (12) |
| | | | | 0.90 (6) |
| [Ag(BEN)$_{0.5}$][Hx$_3$NB$_{12}$F$_{11}$] | TOL-d$_8$ | | −254.2 (1) | |
| | | | −258.4 (5) | |
| | | | −260.5 (5) | |
| Cs[Oc$_3$NB$_{12}$F$_{11}$] | ACN-d$_3$ | −13.4 (1) | −258.9 (5) | 3.36 (6) |
| | | −16.2 (10) | −259.2 (1) | 1.76 (6) |
| | | −27.7 (1) | −262.7 (5) | 1.30 (30) |
| | | | | 0.89 (9) |
| Cs[Dd$_3$NB$_{12}$F$_{11}$] | ACN-d$_3$ | −13.4 (1) | −258.9 (5) | 3.36 (6) |
| | | −16.2 (10) | −259.2 (1) | 1.75 (6) |
| | | −27.7 (1) | −262.7 (5) | 1.31 (6) |
| | | | | 1.28 (48) |
| | | | | 0.88 (9) |
| Cs[Dd$_3$NB$_{12}$F$_{11}$] | acetone-d$_6$ | | −258.1 (1) | |
| | | | −258.9 (5) | |
| | | | −262.0 (0) | |
| Cs[Dd$_3$NB$_{12}$F$_{11}$] | DCM-d$_2$ | | −252.9 (1) | |
| | | | −257.6 (5) | |
| | | | −258.5 (5) | |
| Cs[Dd$_3$NB$_{12}$F$_{11}$] | TOL-d$_8$ | | −252.2 (1) | |
| | | | −257.5 (5) | |
| | | | −258.2 (5) | |
| Li[Dd$_3$NB$_{12}$F$_{11}$] | ACN-d$_3$ | −13.4 | −258.9 (5) | 3.37 (6) |
| | | −16.3 | −259.3 (1) | 1.76 (6) |
| | | −27.8 | −262.8 (5) | 1.29 (54) |
| | | | | 0.88 (9) |
| Li[Dd$_3$NB$_{12}$F$_{11}$] | BEN-d$_3$ | broad | −257.5 (broad) | 3.49 (6) |
| | | | −263.3 (broad) | 1.77 (6) |
| | | | | 1.41 (54) |
| | | | | 0.97 (9) |
| [CPh$_3$][Dd$_3$NB$_{12}$F$_{11}$] | DCM-d$_2$ | | −259.1 (1) | |
| | | | −259.7 (5) | |
| | | | −263.2 (5) | |
| [CPh$_3$][Dd$_2$MeNB$_{12}$F$_{11}$] | DCM-d$_2$ | | −259.4 (1) | |
| | | | −261.2 (5) | |
| | | | −263.6 (5) | |
| [NBu$_3$H][Dd$_2$MeNB$_{12}$F$_{11}$] | TOL-d$_8$ | | −256.6 (1) | 5.79 (1) |
| | | | −258.4 (1) | 3.43 (6) |
| | | | −260.9 (1) | 2.78 (6) |
| | | | | 1.74 (6) |
| | | | | 1.46 (6) |
| | | | | 1.27 (60) |
| | | | | 0.94 (18) |

[a]All spectra at 25° C.; δ ($^{11}$B) for BF$_3$(OEt$_2$) = 0; δ ($^{19}$F) for CFCl$_3$ = 0; $^{19}$F NMR resonances were multiplets with unequal intensities; int. = integrated intensity.

The ion pairing in [NBu$_3$H][Dd$_3$NB$_{12}$F$_{11}$] was weaker than in Cs(Dd$_3$NB$_{12}$F$_{11}$), as indicated by the fact that the $^{19}$F NMR resonances (TOL-d8) of the anion in [NBu$_3$H][Dd$_3$NB$_{12}$F$_{11}$] were less shielded (δ−256.6, −258.4, and −260.9) than in Cs(Dd$_3$NB$_{12}$F$_{11}$) (δ−252.2, −257.5, and −258.2).

Example 18

This example illustrates a method for synthesizing Li(Dd$_3$NB$_{12}$F$_{11}$).

A mixture of [NBu$_4$]$_2$[H$_2$NB$_{12}$F$_{11}$] (0.300 g, 0.358 mmol) and DdBr (3 mL) was refluxed in 0.5 M aqueous KOH for 22 h. The mixture was then refluxed with an additional amount of DdBr (3 mL) for 32 h. The compound [NBu$_4$][Dd$_3$NB$_{12}$F$_{11}$] was extracted with benzene (50 mL). Benzene and other volatile organic compounds were removed by vacuum distillation at 120° C., leaving a light-yellow oil. The oil was washed two times with hexane (2×30 mL) and dried at 120° C. for 18 h. The sticky solid was dissolved in methanol (50 mL). This solution was eluted with methanol through a column packed with Rohm & Haas XN-1010 cation exchange resin in its acidic form. The solution was neutralized with LiOH to about pH 7 and filtered. Methanol was removed from the filtrate under vacuum, leaving an oily residue. The residue was dissolved in pentane (30 mL) and insoluble material (traces of solid) was removed by filtration. Pentane was removed under vacuum and the oily residue was dried under vacuum at 185° C. for 18 h, leaving a tan solid. The yield of Li(Dd$_3$NB$_{12}$F$_{11}$) was 0.131 g (42% based on [NBu$_4$]$_2$[H$_3$NB$_{12}$F$_{11}$]). The yield was low due to the fact that some amount of [NBu$_4$][Dd$_3$NB$_{12}$F$_{11}$] dissolved in hexane during the washing and was not recovered.

The $^{19}$F NMR resonances of the anion of Li(Dd$_3$NB$_{12}$F$_{11}$) were very broad. The compound was extremely hydroscopic. When the NMR sample was briefly exposed to air, the compound [Li(H$_2$O)$_4$][Dd$_3$NB$_{12}$F$_{11}$] was formed. The $^{19}$F NMR resonances of the anion became sharp. It is believed that this change in resolution was probably due to reduced lithium-anion interactions in the salt $[Li(H_2O)_4]$ $[Dd_3NB_{12}F_{11}]$. The compound $Li(Dd_3NB_{12}F_{11})$ was stable at 185° C. for at least 18 h.

Example 19

This example illustrates a method for synthesizing $[CPh_3]$ $[Dd_3NB_{12}F_{11}]$.

A mixture of $Cs(Dd_3NB_{12}F_{11})$ (0.700 g, 0.705 mmol) and $CPh_3BF_4$ (0.233, 0.705 nmmol) was stirred in DCM (30 mL) at 25° C. for 6 h. The insoluble material that formed was removed by filtration through Celite. DCM was removed under vacuum, leaving an orange-brown sticky solid. The solid was washed with ISO (2×20 mL) and dried under vacuum for 18 h. The yield of orange-brown solid $[CPh_3]$ $[Dd_3NB_{12}F_{11}]$ was 0.700 g (90% yield based on $Cs(Dd_3NB_{12}F_{11})$).

Example 20

This example illustrates a method for synthesizing $[NBu_3H][Dd_3NB_{12}F_{11}]$.

A solution of $[H(MeOH)_x][Dd_3NB_{12}F_{11}]$ (see Example 18) was neutralized with $Bu_3N$. Methanol was removed under vacuum leaving a viscous oil. The oil was washed two times with pentane (2×5 mL). The oil was dried under vacuum at 120° C. for 18 h to yield $[NBu_3H][Dd_3NB_{12}F_{11}]$.

Example 21

This example illustrates a method for synthesizing $Li(Bn_2HNB_{12}F_{11})$.

A mixture of $Cs(H_3NB_{12}H_{11})$ (0.50 g, 1.72 mmol) and anhydrous HF (45 mL) was treated with $F_2$ (20.6 mmol, 12 equiv.) for 48 h. Volatiles were removed under vacuum and the solid reaction products were dissolved in 0.5 M aqueous KOH (70 mL). The blue-green precipitate was removed by filtration. The filtrate was refluxed with BnBr (3 mL) and $NBu_4Br$ for 32 h. The mixture was separated and the organic fraction was washed with water. Addition of benzene (50 mL) to the organic fraction resulted in formation of a light-yellow solid. The solid was separated by filtration, dried under vacuum, and dissolved in methanol (50 mL). This solution was eluted with methanol through a column packed with Rohm & Haas XN-1010 cation exchange resin in its acidic form. The solution was neutralized with LiOH to about pH 7 and filtered. Methanol was removed from the filtrate under vacuum, leaving an oily residue. The residue was dried under vacuum ($10^{-5}$ Torr) at 170° C. for 18h. The $^{19}F$ and mass spectra of the light-yellow solid in aqueous HCl (pH~1) and in aqueous $NH_4OH$ (pH~9) indicate that the solid was a mixture of $Li(Bn_2HNB_{12}F_{11})$ (about 90 mol %) and $Li(BnH_2NB_{12}F_{11})$ (about 10 mol %). The combined yield was 0.265 g (30% based on $Cs(H_3NB_{12}H_{11})$).

Example 22

This example shows a method for synthesizing $[NBu_4]$ $[(Mc)_2HNB_{12}F_{11}]$.

A 4:1 mixture of $[NBu_4][H_3NB_{12}F_{11}]$ and $[NBu_4][BF_4]$ (0.68 g) was refluxed with McBr (i.e., cyclohexylmethyl bromide) (2 mL) in 0.5 M aqueous KOH for 18 h. A mixture of a red sticky solid and a colorless solution was formed. The sticky solid was separated by filtration, washed with benzene (30 mL), and redissolved in methanol (60 mL). Slow evaporation of MeOH at 25° C. resulted in the formation of a yellow-orange crystalline solid. The yield of $[NBu_4]$ $[Mc_2HNB_{12}F_{11}]$ was 0.418 g (55% based on $[NBu_4]$ $[H_3NB_{12}F_{11}]$).

Example 23

This example illustrates stability of $H_3NB_{12}F_{11}^{-1}$ anion in an aqueous acid and an aqueous base solutions.

To study the stability $H_3NB_{12}F_{11}^{-1}$ under acidic and basic conditions, samples of $Cs(H_3NB_{12}F_{11})$ (10 mg each) were dissolved in a 20% aqueous DCl (i.e., deuterium chloride) solution and a 0.5 M aqueous NaOH solution. The mixtures were monitored by NMR spectroscopy, and substantially no changes were observed during 18 days. Therefore, $B_{12}F_{11}NH_3^-$ is stable under these conditions.

The $^{19}F$ NMR spectrum of a 0.5 M aqueous NaOH solution of $H_3NB_{12}F_{11}^{-1}$ anion indicated nearly complete deprotonation to $H_2NB_{12}F_{11}^{-2}$ dianion under these conditions. The chemical shift of the fluorine atom antipodal to the $NH_2$ group was −268.3 ppm, about 6 ppm upfield of the −261.9 ppm resonance for the $H_3NB_{12}F_{11}^{-1}$ anion in 20% DCl. No significant differences were observed for NMR spectra of the $H_3NB_{12}F_{11}^{-1}$ anion in $CD_3CN$ or in 20% DCl.

Example 24

This example illustrates oxidative, thermal, and Lewis acid stability of $Dd_3NB_{12}F_{11}^{-1}$ anion.

A cyclic voltammogram of $Cs(Dd_3NB_{12}F_{11})$ (1 mM in $CH_3CN$ with 0.1 M $TBA^+PF_6^-$) indicates that $Dd_3NB_{12}F_{11}^{-1}$ is stable to electrochemical oxidation in $CH_3CN$ up to 2.0 V vs. Ag/AgCl. The thermal stability of $Cs(Dd_3NB_{12}F_{11})$ was determined by differential scanning calorimetry (DSC) and by recording NMR spectra of DSC samples after thermal treatment. The compound $Cs(Dd_3NB_{12}F_{11})$ was heated at 200° C. for 0.5 h in a sealed capsule under a nitrogen atmosphere. No exo- or endothermic events were observed. The sample was recovered from the capsule and dissolved in BEN-d6 (there was no insoluble residue). According to $^1H$ and $^{19}F$ NMR spectra the recovered sample was unchanged $Cs(Dd_3NB_{12}F_{11})$. Note, that $Li(Dd_3NB_{12}F_{11})$ was previously determined to be stable at 185° C. for at least 18 h. When the compound $Cs(Dd_3NB_{12}F_{11})$ was heated to 300° C. for 0.5 h in a sealed under nitrogen atmosphere capsule, several endothermic events were observed between 240° C. and 300° C. The color of the recovered solid had changed from light-yellow to yellow-brown. When the sample was dissolved in BEN-d6, only a small amount of $Cs(Dd_3NB_{12}F_{11})$ was observed in $^1H$ and $^{19}F$ NMR and mass spectra. The major anions observed were $Dd_2HNB_{12}F_{11}^{-1}$ and $DdH_2NB_{12}F_{11}^{-1}$, which may have formed by sequential Hoffman-type degradation reactions similar to the generic reaction shown below:

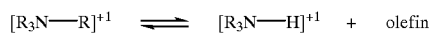

It was also determined that $Dd_3NB_{12}F_{11}^{-1}$ is stable when treated with an excess $AlEt_3$ in toluene. The $^1H$ and $^{19}F$ NMR spectra of $Cs(Dd_3NB_{12}F_{11})$ and its mixtures with 3 and 100 equiv. of $AlEt_3$ in toluene-d8 were virtually identical except for the resonances due to $AlEt_3$.

Example 25

This example illustrates conductivity of $LiB_{12}F_{11}NMe_3$.

A calibrated Yellow Springs model 3403 conductivity cell (cell constant k=1.113) and a model 31 conductivity bridge were employed. The measurements were made in a nitrogen-filled glove box. The conductivity of a 0.010 M glyme solution of $CsB_{12}F_{11}NMe_3$ was found to be 34 $\mu S\ cm^{-1}$. The conductivity of a 0.0050 M glyme solution of $LiB_{12}F_{11}NMe_3$ was found to be 39 $\mu S\ cm^{-1}$. The concentration dependence of the conductivity of a lithium salt in a dilute solution is expected to be linear. The conductivity of a 0.01 M glyme solution of $LiB_{12}F_{11}NMe_3$ is therefore expected to be about 78 $\mu S\ cm^{-1}$. The conductivity of a 0.0050 M glyme solution $LiB_{12}F_{11}NMe_3$ is approximately ten times higher than the conductivity of a 0.010 M glyme solution of lithium triflate (4 $\mu S$ cm–1).

Example 26

This example illustrates conductivities of solutions of $Li(R_xH_{(3-x)}NB_{12}F_{11})$, where x=2 or 3 and R=Me, Bn, or Dd.

The conductivities of solutions of $Li(Dd_3NB_{12}F_{11})$ and $Li(Bn_2HNB_{12}F_{11})$ (the latter sample was contaminated with about 15% $Li(BnH_2NB_{12}F_{11})$) were measured using a similar procedure as that of Example 25. A calibrated Yellow Springs model 3403 conductivity cell (cell constant k=0.98 cm–1) and a Yellow Springs model 31 conductivity bridge was employed. The measurements were made in a nitrogen-filled glove box. The conductivities of glyme solutions of $Li(Dd_3NB_{12}F_{11})$, $Li(Bn_2HNB_{12}F_{11})$, and lithium salts of related anions are listed in Table 2.

TABLE 2

Conductivities of Lithium Salts (0.0100 M DME solutions, 25° C., nitrogen atm.)

| anion | conductivity, $\mu S$ cm–1 |
|---|---|
| $CF_3SO_3^-$ | 4 |
| $Dd_3NB_{12}F_{11}^-$ | 54 |
| $CB_{12}H_{11}^-$ | 59 |
| $Bn_2HNB_{12}F_{11}^-$ | 67 |
| $PF_6^-$ | 73 |
| $Me_3NB_{12}F_{11}^-$ | 78 (39 × 2)[a] |
| 12-$CB_{11}H_{11}F^-$ | 85 |
| 1-Me-$CB_{11}H_{11}^-$ | 190 |

[a]This conductivity was not determined directly; the experimental value Λ = 39 $\mu S\ cm^{-1}$ for a 0.0050 M DME solution of this lithium salt was multiplied by 2.[001b]

The conductivities of $Li(R_xH_{(3-x)}NB_{12}F_{11})$ solutions, Λ=54–78 $\mu S\ cm^{-1}$, were more than ten times higher than the conductivity of an equimolar glyme solution of $LiCF_3SO_3$, Λ=4 $\mu S\ cm^{-1}$, and were similar to the conductivities of $Li^{+1}$ salts of the other weakly coordinating monoanions such as $Li(CB_{11}H_{12})$ (Λ=59 $\mu S\ cm^{-1}$), $LiPF_6$ (Λ=73 $\mu cm^{-1}$), and $Li(12$-$CB_{11}H_{11}F)$ (Λ=85 $\mu S\ cm^{-1}$). Without wishing to be bound by any theory, it is believed that the conductivities of $Li(Dd_3NB_{12}F_{11})$ and $Li(Me_3NB_{12}F_{11})$ suggest that the greater mass and size of the $Dd_3NB_{12}F_{11}^{-1}$ anion relative to the $Me_3NB_{12}F_{11}^{-1}$ anion result in decreased mobility, and therefore decreased conductivity for the lithium salt of the larger anion.

Example 27

This example illustrates interactions of $R_3NB_{12}F_{11}^{-1}$ anions (R=Hx, Oc, Dd) with $SiR_3^{+1}$ species.

To investigate the reactivity and coordinating abilities of $R_3NB_{12}F_{11}^{-1}$ anions (R=Hx, Oc, Dd), we have synthesized $Si(i$-$Pr)_3(R_3NB_{12}F_{11})$ compounds by the reaction shown below:

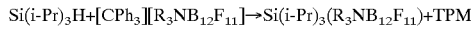

When $[CPh_3][Oc_3NB_{12}F_{11}]$ was treated with $Si(i$-$Pr)_3H$ in ACN-$d_3$, the compounds $[Si(i$-$Pr)_3(ACN)][Oc_3NB_{12}F_{11}]$ and TPM (i.e., triphenyl methane) were formed. The $^{19}F$ NMR signals of the anion were the same as $^{19}F$ NMR signals of the free $Oc_3NB_{12}F_{11}^{-1}$ anion (such as in [TBA][$Oc_3NB_{12}F_{11}$]). When $[CPh_3][Dd_3NB_{12}F_{11}]$ was treated with $Si(i$-$Pr)_3H$ in DCM-$d_2$, no starting materials were observed in the mixture after 10 min. The $^{19}F$ NMR resonances for the antipodal and lower-belt fluorine atoms of the anion were slightly broadened relative to the resonance for the upper-belt fluorine atoms of the anion. The compound $Si(i$-$Pr_3)(Dd_3NB_{12}F_{11})$ decomposed in DCM-$d_2$ (but only after several hours) as indicated by the fact that $^{19}F$ NM resonances of the anion after 19 h were the same as $^{19}F$ NMR resonances of the free $Dd_3NB_{12}F_{11}^{-1}$ anion. The fact that a small amount of $Si(i$-$Pr_3)(Dd_3NB_{12}F_{11})$ was still present in the reaction mixture after 10 min indicates that $Si(i$-$Pr_3)(Dd_3NB_{12}F_{11})$ is less reactive than $Si(i$-$Pr)_3(1$-$Et$-$CB_{11}F_{11})$, which suggests that the $Dd_3NB_{12}F_{11}^{-1}$ anion coordinates more strongly to $Si(i$-$Pr_3)^{+1}$ than the 1-Et-$CB_{11}F_{11}^-$ anion. The $^1H$ NMR spectrum of the reaction solution indicated that a mixture of DPM and TPM was formed after 10 min. However, DPM and TPM subsequently decomposed during 19 h. The major decomposition product was BEN and its derivatives.

It appears that $Dd_3NB_{12}F_{11}^{-1}$ is stable when coordinated to the highly electrophilic $Si(i$-$Pr)_3^{+1}$ cation. Several sharp $^{19}F$ NMR signals from species other than $Dd_3NB_{12}F_{11}^{-1}$ were observed in spectra of reaction solutions after 20 min and 19 h. However, their total integrated intensity did not exceed 10–15%. The same impurities (but only <5%) were rapidly formed when $[CPh_3][R_3NB_{12}F_{11}]$ was treated with 3 equiv. of $Si(i$-$Pr)_3H$ in TOL-$d_8$. The amount of these impurities did not increase over a period of 2 days. The $^{19}F$ NMR signals for $Si(i$-$Pr)_3(R_3NB_{12}F_{11})$ did not change for the same period of time. These facts suggest that $Si(i$-$Pr)_3(Dd_3NB_{12}F_{11})$ and $Si(i$-$Pr)_3(Dd_2MeNB_{12}F_{11})$ are stable in TOL for days. The $^1H$ NMR spectrum no fast exchange of $H^{-1}$ and $Dm_3NB_{12}F_{11}^{-1}$ anions in the mixture of $Si(i$-$Pr)_3H$ and $Si(i$-$Pr)_3(Dm_3NB_{12}F_{11})$. Without being bound by any theory, it is believed that this may be due to the higher electrophilicity of the silicon atom in $Si(i$-$Pr)_3(1$-$Et$-$CB_{11}F_{11})$ relative to the silicon atom in $Si(i$-$Pr)_3(R_3NB_{12}F_{11})$. The smaller δ($^1H$) value for the isopropyl methyl groups in $Si(i$-$Pr)_3(R_3NB_{12}F_{11})$, 0.86, relative to the value for $Si(i$-$Pr)_3(1$-$Et$-$CB_{11}F_{11})$, 0.75, also suggeests that silicon atom is more electrophilic in $Si(i$-$Pr)_3(1$-$Et$-$CB_{11}F_{11})$ than in $Si(i$-$Pr)_3(R_3NB_{12}F_{11})$.

The compound $Si(i$-$Pr)_3(Dd_3NB_{12}F_{11})$ exists as two linkage isomers in toluene solution. At 25° C., the $^{19}F$ NMR signals from the antipodal and lower-belt fluorine atoms were very broad relative to the signal for the upper-belt fluorine atoms. At –70° C., two different species were observed. The more abundant species (90%) exhibited a 1:5:5 $^{19}F$ intensity pattern which suggests coordination of the anion to the silicon center via its antipodal fluorine atom. The less abundant species (10%) exhibited an approximately 1:1:2:2:2:1 $^{19}F$ intensity pattern which suggests coordination of the anion to the silicon center via one of its lower-belt fluorine atoms.

Example 28

This example shows coordination of $R_3NB_{12}F_{11}^-$(R=Hx, Oc, Dd) to Cationic Zirconocenes.

Cation-like zirconocene complexes with trialkylaminofluoroborate anions were generated by the reactions shown below:

$ZfMe_2+[CPh_3][Me_3NB_{12}F_{11}] \rightarrow ZfMe(Me_3NB_{12}F_{11})+TPE$
$ZpMe_2+[CPh_3][Hx_3NB_{12}F_{11}] \rightarrow ZpMe(Hx_3NB_{12}F_{11})+TPE$
$ZpMe_2+[CPh_3][R_3NB_{12}F_{11}] \rightarrow ZpMe(R_3NB_{12}F_{11})+TPE$ ZpMe$_2$+[Bu$_3$NH][Dd$_3$NB$_{12}$F$_{11}$]→ZpMe(Dd$_3$NB$_{12}$F$_{11}$)+ Bu$_3$N+MeH

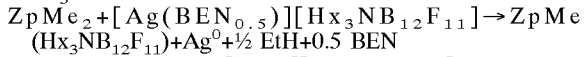

The compounds [CPh$_3$][Me$_3$NB$_{12}$F$_{11}$] and ZfMe (Me$_3$NB$_{12}$F$_{11}$) were not soluble in aromatic hydrocarbon solvents. When a yellow TOL-d$_8$ solution of ZfMe$_2$ was added to a suspension of the yellow solid [CPh$_3$] [Me$_3$NB$_{12}$F$_{11}$] in TOL-d$_8$, no visible change in the reaction mixture was observed during 0.5 h. A $^1$H NMR spectrum of the mixture indicated that less than 3% of the expected amount of TPE had formed. When the reaction mixture was heated to 55° C. for 18 h, the yellow solid became red in color. A $^1$H NMR spectrum of the mixture at this time indicated that more TPE had formed. However, a $^{19}$F NMR spectrum of the reaction mixture indicated that no fluorine-containing species were present in solution. The red solid was separated from the TOL-d$_8$ solution and was redissolved in ACN-d$_3$. The red ACN-d$_3$ solution became orange after 2 h. Proton and $^{19}$F NMR spectra of the orange ACN-d$_3$ solution indicated the presence of free Me$_3$NB$_{12}$F$_{11}$$^{-1}$, which was stable in the presence of the putative zirconocene complex ZfMe(ACN)$^{+1}$.

The compounds [CPh$_3$][Me$_3$NB$_{12}$F$_{11}$] and ZfMe (Me$_3$NB$_{12}$F$_{11}$) were sparingly soluble in DCM-d$_2$, but ZfNe (Me$_3$NB$_{12}$F$_{11}$) decomposed in DCM-d$_2$ during several hours. When 0.5 mL of a yellow DCM-d$_2$ solution of ZNe$_2$ (2.0 mg, 4.0 µmol) was added to a 0.5 mL of a yellow DCM-d$_2$ solution of [CPh$_3$][Me$_3$NB$_{12}$F$_{11}$] (2.0 mg, 3.1 µmol), a red-brown solution was formed. A quantitative $^1$H NMR spectrum of the reaction solution indicated that all of the CPh$_3$$^{+1}$ cation was converted to TPE within 15 min. A dark solid started to precipitate from the reaction mixture after 1.5 h at 25° C. The concentration of the anion decreased by a factor of about four after 2.5 h, and no $^1$H NMR signals for the anion or for the fluorenyl ligand were observed after 23 h. The dark solid that formed during that period of time was redissolved in ACN-d$_3$. The $^1$H NMR and mass spectrum of the solution indicated the presence of free Me$_3$NB$_{12}$F$_{11}$$^{-1}$.

The compounds [Ag(C$_6$H$_6$)$_{0.5}$][Hx$_3$NB$_{12}$F$_{11}$], [CPh$_3$] [Hx$_3$NB$_{12}$F$_{11}$], and ZpMe(Hx$_3$NB$_{12}$F$_{11}$) were soluble to greater than 20 mM in aromatic hydrocarbon solvents but were insoluble in aliphatic hydrocarbons. When a colorless TOL-d$_8$ solution of ZpMe$_2$ (4.8 mg, 20 µmol) was added to a light yellow TOL-d$_8$ solution of [Ag(C$_6$H$_6$)$_{0.5}$] [Hx$_3$NB$_{12}$F$_{11}$] (15.0 mg, 19.9 µmol), a mixture of a black solid a yellow-orange solution was formed. The black solid was removed by filtration. The $^1$H NMR spectrum of the filtrate exhibited Cp resonances at δ 5.95 (rel. int.=6.9) and at δ 6.39 (rel. int.=1.3), indicating the formation of cation-like zirconocene complexes. The ZrMe resonances were not directly observed due to the overlap of their resonances with Me resonances of the anion (δ~0.86). When another equiv. of ZpMe2 was added to the solution, only one Cp signal (δ 5.75) and only one broad Me signal (δ 0.01) were observed for the zirconocene complexes. The $^{19}$F NMR resonance for the antipodal fluorine atom in ZpMe(Hx$_3$NB$_{12}$F$_{11}$), at δ–248.8, was broadened and shielded relative to the corresponding resonance for the antipodal fluorine atom in [Ag (C$_6$H$_6$)$_{0.5}$][Hx$_3$NB$_{12}$F$_{11}$], at δ–254.2, indicating stronger ion-pairing coordination) in the zirconium compound than in the silver compound. The $^{19}$F NMR resonances for the lower-belt fluorine atoms in ZpMe(Hx$_3$NB$_{12}$F$^{11}$) were broader than the resonances for the upper-belt fluorine atoms, indicating the presence of at least two linkage isomers (i.e., an antipodal isomer and a lower-belt isomer). When additional amounts ZpMe$_2$ were successively added to the TOL-d$_8$ solution of ZpMe(Hx$_3$NB$_{12}$F$_{11}$), the resonances for the antipodal fluorine atom were deshielded and became sharper. However, even after the addition of 6 equiv. of ZpMe$_2$, the $^{19}$F regonnee for the antipodal fluonl atom, at δ–250.2, was still broader and was deshielded relative to the corresponding resonance in Cs(Hx$_3$NB$_{12}$F$_{11}$) (δ–252.0), [Ag(C$_6$H$_6$)$_{0.5}$][Hx$_3$NB$_{12}$F$_{11}$] (δ–254.2), or [N(n-Bu)$_3$H] [Dd$_3$NB$_{12}$F$_{11}$] (δ–256.6). These results indicate that the equilibrium constant for the reaction shown below, while not vanishingly small, is considerably less than 1:

The yellow-orange compound [CPh$_3$][Hx$_3$NB$_{12}$F$_{11}$] is not soluble in MCH-d$_{14}$. Nevertheless, it reacted slowly with ZpMe$_2$ dissolved in MCH-d$_{14}$. When a colorless MCH-d$_{14}$ solution of ZpMe$_2$ was added to solid [CPh$_3$][Hx$_3$NB$_{12}$F$_{11}$], no obvious changes were observed in the reaction mixture for 0.5 h. However, a quantitative $^1$H NMR spectrum, indicated that 5% of the expected amount of TPE had formed during the 15 min. After the reaction mixture was heated to 70° C. for 1 h, ~50%) of the expected amount of TPE had formed. By that time, the yellow-orange solid had became orange-red, but the supernatant was colorless. When TOL was added to the reaction solution (MCH-d$_8$/TOL=1:1) a slightly yellow solution and an orange solid were formed. A $^1$H NMR spectrum of this mixture indicated that all of the CPh$_3$$^{+1}$ cation had been converted into TPE. A small amount of ZpMe(Hx$_3$NB$_{12}$F$_{11}$) was present in the solution. The orange solid completely redissolved in TOL-d$_8$. The $^1$H and $^{19}$F NMR spectra of this solution were very similar to the spectra of ZpMe(Hx$_3$NB$_{12}$F$_{11}$), generated in situ from [Ag (BEN$_{0.5}$)][Hx$_3$NB$_{12}$F$_{11}$].

Cation-like zirconocene complexes of trialkylaminofluoroborate anions that are soluble in aliphatic hydrocarbon solvents were generated from ZpMe$_2$ and either [CPh$_3$] [R$_3$NB$_{12}$F$_{11}$] or [NBu$_3$H][Dd$_3$NB$_{12}$F$_{11}$]. The $^{19}$F NMR spectrum of ZpMe(Dd$_3$NB$_{12}$F$^{11}$) generated in situ from ZpMe$_2$ and [NBu$_3$H][Dd$_3$NB$_{12}$F$_{11}$] in ISO exhibited broad $^{19}$F NMR resonances for the antipodal and the lower-belt fluorine atoms of Dd$_3$NB$_{12}$F$_{11}$$^{-1}$, indicating strong ion-pairing (i.e., coordination) between Dd$_3$NB$_{12}$F$_{11}$$^{-1}$ and ZpMe$^{+1}$.

When 0.5 mL of a colorless MCH-d$_{14}$ solution of ZpMe$_2$ (2.1 mg, 8.7 µmol) was added to a suspension of the sticky orange solid [CPh$_3$][R$_3$NB$_{12}$F$_{11}$] (9.0 mg, 8.7 µmol) in 0.5 mL of MCH-d$_{14}$, a homogeneous, dark-orange solution formed within two minutes. This indicates that both ZpMe (Dd$_3$NB$_{12}$F$_{11}$) and ZpMe(Dd$_2$MeNB$_{12}$F$_{11}$) are soluble in MCH-d$_{14}$. The $^1$H and $^{19}$F NMR resonances of the anions were broad. To probe the solubility of hydride zirconocene complexes such as ZpH(R$_3$NB$_2$F$_{11}$) in MCH-d$_{14}$, 1 atm of H$_2$ was added to the reaction solution. The dark-orange solution became light yellow-orange in color. The $^{19}$F and $^1$H NMR resonances of the anion became even broader than before.

The reactions of [CPh$_3$][R$_3$NB$_{12}$F$_{11}$] and [NBu$_3$H][Dd$_3$NB$_{12}$F$_{11}$] with AlEt$_3$ was also investigated. The compounds AlR$_3$ and (AlOR)$_x$ are often used as co-catalysts and water scavengers in metallocene-catalyzed olefin-polymerization processes. When a TOL-d$_8$ solution of [NBu$_3$H][Dd$_3$NB$_{12}$F$_{11}$] (22.0 mg) was treated with ~7 equiv. of AlEt$_3$, the formation of gas bubbles, presumably EtH, was observed immediately. The NH $^1$H NMR resonance of the NBu$_{3H+1}$ cation decreased in intensity by about a factor of three. The $^1$H NMR spectrum after 22 h indicated the presence of NBu$_3$ (δ 2.43) and either NBu$_3$H$^{+1}$ or coordinated NBu$_3$ (δ 2.61). The $^{19}$F NMR resonances for the antipodal and lower-belt fluorine atoms of the anion were broad compared to those for the upper-belt fluorine atoms. This is believed to be due to the coordination of Dd$_3$NB$_{12}$F$_{11}$$^{-1}$ to an electrophilic, cation-like aluminum species generated in the reaction of AlEt$_3$ with NBu$_3$H$^{+1}$. The solution was then treated with ZpMe$_2$ (5.1 mg) and the colorless solution became yellow-orange in color. The $^1$H NMR spectrum indicated the presence of free Bu$_3$N (δ~2.43 ppm). The $^1$H NMR spectra also exhibited two Cp signals at δ 5.95 (rel. int.=7.4) and 5.18 (rel. int.=1.91). It is possible the Cp resonance at δ 5.18 may be due to the putative zirconocene complex ZpMe(MeAlEt$_3$). The methyl $^1$H NMR resonance was observed at δ−0.02. The $^{19}$F NMR spectrum exhibits broad resonances for the fluorine atoms of the anion, including a resonance for the antipodal fluorine atom with an unusually large upfield chemical shift (δ−292). When about 6 equiv. of THF were added to the yellow-orange reaction solution, the solution became light yellow. The $^{19}$F NMR spectrum exhibited a 1:5:5 intensity pattern with chemical shifts almost identical to those of [NBu$_3$H][Dd$_3$NB$_{12}$F$_{11}$]. However, the resonances for the antipodal and lower-belt fluorine atoms were slightly broadened compared with the multiplet for the upper-belt fluorine atoms. This may be due to outer-sphere ion-pairing between Dd$_3$NB$_{12}$F$_{11}$$^{-1}$ and ZpMe(THF)$^{+1}$. Note that the Dd$_3$NB$_{12}$F$_{11}$$^{-1}$ anion was stable in the presence of highly electrophilic cation-like aluminum and zirconocene species for at least several days at 25° C.

When an orange-brown TOL-d$_8$ solution of [CPh$_3$][R$_3$NB$_{12}$F$_{11}$] was treated with about 5 equiv. of AlEt$_3$, the solution became light tan within a few minutes. The $^1$H NMR spectra indicated the formation of TPM (about 0.6 equiv.). There were also a singlet at 5.26 ppm, which can be puftatively assigned to C$_2$H$_4$ (δ(C$_2$H$_4$)=5.2). It is possible that [CPh$_3$][R$_3$NB$_{12}$F$_{11}$] reacts with AlEt$_3$ via a β-hydride abstraction by the reaction shown below:

[CPh$_3$][R$_3$NB$_{12}$F$_{11}$]+AlEt$_3$→[AlEt$_2$(η$^2$-C$_2$H$_4$)][R$_3$NB$_{12}$F$_{11}$]+TPM

The $^{19}$F NMR spectrum of the reaction solution exhibited deshielded broad resonances for the antipodal and the lower belt fluorine atoms of the anion. This is believed to be due to interactions between R$_3$NB$_{12}$F$_{11}$$^{-1}$ and one or more cation-like aluminum complexes. When the tan solution was treated with ZpMe$_2$, the solution became yellow-orange in color. The $^1$H and $^{19}$F NMR spectra were similar to the spectra of ZpMe(Dd$_3$NB$_{12}$F$_{11}$), generated in situ from a mixture of [NBu$_3$H][Dd$_3$NB$_{12}$F$_{11}$], AlEt$_3$, and ZpMe$_2$. These results indicate that both [CPh$_3$][Dd$_3$NB$_{12}$F$_{11}$] and [NBu$_3$H][Dd$_3$NB$_{12}$F$_{11}$] react with AlEt$_3$ to form one or more cation-like aluminum complexes. The cation-like aluminum complex(es) reacted further with ZpMe$_2$ with the formation of cation-like-zirconocene complexes.

Example 29

This example illustrates Bronsted acidity of H$_3$NB$_{12}$F$_{11}$$^-$.

The anion H$_3$NB$_{12}$F$_{11}$$^{-1}$ is a weak Bronsted acid in aqueous solution according to the following equation:

The "protonated" (H$_3$NB$_{12}$F$_{11}$$^{-1}$) and "deprotonated" (H$_2$NB$_{12}$F$_{11}$$^{-2}$) forms of H$_3$NB$_{12}$F$_{11}$$^{-1}$ have different $^{19}$F NMR chemical shifts. Nevertheless, only one set of 1:5:5 signals was observed in $^{19}$F NMR spectra of aqueous solutions of Cs(H$_3$NB$_{12}$F$_{11}$) in the pH range 0–14. Without being bound by any theory, it is believed this is due to a fast exchange between the protonated and deprotonated forms of the two ammonioborate anions under these conditions.

To determine the pKa value of H$_3$NB$_{12}$F$_{11}$$^-$, a series of solutions of Cs(H$_3$NB$_{12}$F$_{11}$) in aqueous buffer were prepared and $^{19}$F NMR spectra of these solutions were recorded. The data are listed in Table 3.

TABLE 3

Fluorine-19 chemical shifts and derived mole % values for mixtures of H$_3$NB$_{12}$F$_{11}$$^{-1}$ and H$_3$NB$_{12}$F$_{11}$$^{-2}$ in aqueous buffer

| pH | δ ($^{19}$F), upper or lower belt | δ ($^{19}$F), lower or lower belt | δ ($^{19}$F), antipodal position | mole % H$_3$NB$_{12}$F$_{11}$$^{-1}$ | mole % H$_2$NB$_{12}$F$_{11}$$^{-2}$ |
|---|---|---|---|---|---|
| 0.00 | −262.18 | −267.64 | −261.91 | 100 | 0 |
| 7.25 | −263.15 | −268.80 | −263.15 | 80.2 | 19.8 |
| 9.31 | −263.45 | −268.36 | −264.36 | 61.1 | 38.9 |
| 9.87 | −264.08 | −268.08 | −266.15 | 32.7 | 67.3 |
| 10.36 | −264.29 | −267.86 | −266.93 | 20.1 | 79.9 |
| 12.62 | −264.72 | −267.56 | −268.25 | 0 | 100 |
| 14.00 | −264.58 | −267.50 | −268.20 | 0 | 100 |

Here and elsewhere, the $^{19}$F NMR chemical shift standard was CFCl$_3$ (δ 0). Relative concentrations of H$_3$NB$_{12}$F$_{11}$$^{-1}$ and H$_2$NB$_{12}$F$_{11}$$^{-2}$ were calculated based on the average δ value for the antipodal fluorine atom and the limiting δ values at high and low pH, and these are also listed in Table 1. The pKa value was determined to be 9.7 using the following equation:

$$pK_a = pH + \log\left[\frac{\text{mole\%  H}_3\text{NB}_{11}\text{F}_{11}^-}{\text{mole\%  H}_2\text{NB}_{11}\text{F}_{11}^{2-}}\right]$$

Bronsted acidities (pKa values) of relevant species are listed in Table 4. Note that the acidity of the H$_3$NB$_{12}$F$_{11}$$^{-1}$ anion is comparable to that of NH$_4$$^+$.

TABLE 4 pKa Values of Selected Acids and H3NB12F11–, and 1-H-CB11F11–

| Bronsted acid species | pKa value |
|---|---|
| HSO$_4$$^{-1}$ | 1.9 |
| NH$_2$Ph$^{+1}$ | 4.6 |
| NH$_4$$^{+1}$ | 9.3 |
| H$_3$NB$_{12}$F$_{11}$$^{-1}$ | 9.7 |
| HCO$_3$ | 10.3 |
| NH$_3$Me$^{+1}$ | 10.7 |
| NH3Bu$^{+1}$ | 10.8 |
| HS$^{-1}$ | 19.0 |

Example 30

This example illustrates a method for producing Cs(Me$_3$NB$_{12}$F$_{11}$).

A mixture of Cs(H$_3$NB$_{12}$H$_{11}$) (0.800 g, 2.753 mmol) and anhydrous HF (55 ml) was treated with a 20% F$_2$/N$_2$ mixture (33.0 mmol of $F_2$) for 48 hours. All volatiles were then removed under vacuum and the remaining solid was dissolved in 80 mL of 0.5 M KOH solution. A blue-green precipitate that formed was removed by filtration. The filtrate was placed under vacuum to remove traces of $NH_3$. It is believed that $NH_3$ is formed due to the hydrolysis of $NH_4BF_4$, which is a possible side-product in fluorination of $Cs(H_3NB_{12}H_{11})$. The filtrate was treated with I mL of $(MeO)_2SO_2$ (1.33 g, 10.60 mmol) for two hours. A white precipitate that formed was collected by filtration, washed two times with 10 mL of water and dried under vacuum at 100° C. for 24 hours. The yield of $Cs(Me_3NB_{12}F_{11})$ was 0.398 g (27% based on $Cs(H_3NB_{12}H_{11})$).

Example 31

This example illustrates a method for producing $[CPh_3][Me_3NB_{12}F_{11}]$.

A solution of $Cs(Me_3NB_{12}F_{11})$ (0.392 g, 0.739 mmol) in 10 mL of acetonitrile was treated with a solution of $AgBF_4$ (0.145 g, 0.744 mmol) in 5 mL of acetonitrile. A white precipitate that formed ($CsBF_4$) was removed by filtration and a filtrate was treated with a solution of $CPh_3Cl$ (0.208 g, 0.747 mmol) for one hour. The insoluble material was removed by filtration and acetonitrile was removed under vacuum. The yellow solid was collected and washed two times with 2 mL of dichloromethane. The solid was redissolved in 200 ml of dichloromethane and insoluble material ($CsBF_4$) was removed by filtration. Dichloromethane was removed under vacuum to yield 0.378 g of yellow $[CPh_3][Me_3NB_{12}F_{11}]$ (80% yield based on $Cs(Me_3NB_{12}F_{11})$).

Example 32

This example illustrates a method for producing $Si(i-Pr)_3(Me_3NB_{12}F_{11})$.

A compound $[CPh_3][Me_3NB_{12}F_{11}]$ (0.323 g, 0.504 mmol) was treated with 5 mL of $Si(i-Pr)_3H$ for 3 days at 60° C. A light yellow solid was separated by filtration, washed three times with 2 mL of hexanes and dried under vacuum. The yield of $Si(i-Pr)_3(Me_3NB_{12}F_{11})$ was 0.215 g (77% yield based on $[CPh3][Me_3NB_{12}F_{11}]$).

$^1$H NMR (acetonitrile-$d_3$): δ 1.18 (18 H), 1.49 (3 H), 3.15 (9 H);

$^{19}$F NMR (acetonitrile-$d_3$): δ−259.1 (1 F), −262.7 (10 F).

Example 33

This example illustrates ability of aminoborate compounds as olefin polymerization catalyst activators.

All solvents used in synthesis and polymerization experiments were obtained when possible as anhydrous grade and further purified as described below. Diethyl ether, hexanes and toluene were obtained from Aldrich Chemical Company (Milwaukee, Wis.) in Sure Seal® bottles as anhydrous grade. Solvents were further purified by passing through columns packed with activated A2 alumina and Q-5 catalyst which had been reduced tbennally under hydrogen. Methylliium in aiethyl ether, zirconecene dichloride, pentamethylcyclopentadienyl zirconium dichloride and methylaluminoxane (10 wt. % in toluene) were obtained from Aldrich Chemical Company and used without further purification. Methyllithium was titrated with an aqueous HCl standard (Aldrich Chemical Company) against a phenolphthalein indicator in order to determine the concentration prior to use. Tris(perfluorophenyl)borate (i.e., B2 borate) was obtained as a research sample from Albermarle (Baton Rouge, La.) (Lot # 29779501-10) and used without further purification.

The solvent for polymerization experiments was 2,2,4-trimethylpentane (i.e., iso-octane) which was obtained from Aldrich Chemical Company in 18 L Stainless Steel Kilo Lab® Cylinders as anhydrous grade. The polymerization solvent was further purified by passing through columns packed with activated 13× molecular sieves and Q-5 catalyst. Periodic checks were performed on the water content of the solvent by Karl Fischer Columbmetric Titration and determined to contain 3 ppm or less water after purification. Solids were stored, weighed and transferred in glove box equipped with a catalyst train under dry nitrogen. Polymerization stock solutions and compositions were prepared in septum fitted bottles in a glove box. All solutions were freshly prepared for each set of evaluations.

Preparation of dimethyizirconecene

Dimethylzirconecene was prepared by a previously described method reported by Samuel and Rausch, *J. Am. Chem. Soc.*, 1973, 95, 6263. $Cp_2ZrCl_2$ (3.101 g, 10.61 mmol) was weighed in a glove box into a 250-mL Schlenk flask and transferred to a vacuum/nitrogen synthesis line. To the flask was added diethyl ether (80 mL), which slurried the solid. The flask was fitted with a 125 mL pressure equalizing dropping funnel which was nitrogen purged. To the dropping funnel was added diethyl ether (40 mL), then methyllithium solution (13.3 mL of a 1.60 M solution in diethyl ether, 21.22 mmol) was added. The contents of the flask were cooled to −50° C. to −55° C. during the addition of methyllithium which was added over period of about 45 minutes. A lightly colored voluminous precipitate formed. The mixture was allowed to slowly warm to room temperature while stirring overnight. A light tan solid with a nearly clear solution remained. Volatiles were removed under vacuum leaving a light tan colored solid. The solid was transferred into sublimation apparatus in a glove box then transferred back to a vacuum/nitrogen synthesis line. The sublimator was heated under vacuum in an oil bath, solid started to sublime once the temperature reached about 60° C. The temperature was gradually increased over 1 hour to about 80° C. after which no additional sublimation was observed (the prove was cooled to −78° C). A nearly white solid was obtained on the probe, which was harvested in a glove box and transferred to a vial for storage. A total of 1.169 g (4.65 mmol) of product was recovered for an overall yield of 44% based on Zr.

Preparation of $Cp_2ZrMe_2$ solution.

All solutions were prepared in a glove box under dry nitrogen in a glass narrow mouth bottle fitted with a septum. This solution was prepared by the dissolution of 63 mg of $Cp_2ZrMe_2$ in 50 mL of dry, nitrogen degassed toluene. The complex was completely miscible in the solvent. The concentration of $Cp_2ZrMe_2$ was about 5 μmole/mL in Zr.

Preparation of B2 borate solution

The solution was prepared by the dissolution of 512 mg of B2 borate in 50 mL of toluene. The concentration was about 20 μmole/mL in boron.

Preparation of 1% Methylaluminoxane (MAO) solution.

A stock solution with a concentration of 10 wt % in toluene was diluted to 1 wt % (about 199 μmole/mL in Al) in toluene. This was prepared by the addition of 5 mL of the stock solution to 45 mL of toluene. For most experiments, the stock solution as used without flrther dilution.

Table I shows results of olefin polymerization using $[CPh_3][Dd_3NB_{12}F_{11}]$ with $Cp_2ZrMe_2$ and MAO versus B2 borate.

TABLE I

Olefin polymerization using [CPh₃][Dd₃NB₁₂F₁₁] with Cp₂ZrMe₂ and MAO versus B2 Borate.

| [Zr]/Type[1] μmole | Zr/A/A1[2] (A = anion) | Max Rate C₂H₄ uptake (g/m @ m:ss) | Max Exotherm (° C. @ m:ss) | Final Rate C₂H₄ uptake (g/m) | Polymer Dry Wt. (g) | Polym. Efficiency (kg-P/g-Zr) |
|---|---|---|---|---|---|---|
| 20/C | 1/4/250 | 24.9 @ 1:01 | 2 @ 0:12 | 0.8 | 42.5 | 23.3 |
| 20/C | 1/4/250 | 31.3 @ 0:44 | 2 @ 0:09 | 0.8 | 65.5 | 35.9 |
| 20/E | 1/4/250 | 20.3 @ 1:01 | 1 @ 0:06 | 0.7 | 40.0 | 21.9 |
| 20/E | 1/4/250 | 21.0 @ 1:15 | 2 @ 0:12 | 0.7 | 34.0 | 18.6 |
| 20/C | 1/4/250 | 26.3 @ 0:39 | 1 @ 0:08 | 0.7 | 53.5 | 29.3 |
| 20/C | 1/4/250 | 21.7 @ 0:59 | 2 @ 0:09 | 0.9 | 74.5 | 40.8 |
| 20/C | 1/4/250 | 16.3 @ 0:39 | 2 @ 0:08 | 1.3 | 91.5 | 49.6 |

[1]C = control (i.e., B2 borate), E = Experimental (i.e., [CPh₃][Dd₃NB₁₂F₁₁])
[2]Zr = zironocene, A = anion, A1 = MAO All publications, patents, and patent applications cited herein are hereby incorporated by reference in their entirety for all purposes. In addition, the foregoing discussion of the invention has been presented for purposes of illustration and description, which is not intended to limit the present invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound comprising a fluorinated polyhedral borate monoanion of the formula $[R^1R^2R^3N—B_aH_bF_c]^{-1}$, wherein $R^1$, $R^2$, and $R^3$ are bonded to N, and N is bonded to boron, and each of H and F is bonded to a different boron atom, and wherein
   each of $R^1$, $R^2$, and $R^3$ is independently selected from the group consisting of hydrogen, $C_1$–$C_{20}$ alkyl, $C_3$–$C_{10}$ cycloalkyl, $C_6$–$C_{20}$ aryl, $C_7$–$C_{20}$ aralkyl, haloalkyl, alkenyl, polymer, and silyl;
   a is an integer from 6 to 14;
   b is an integer from 0 to 12; and
   c is an integer from 1 to 13, provided the sum of 1+b+c is a.

2. The compound of claim 1, wherein each of $R^1$, $R^2$, and $R^3$ is independently selected from the group consisting of hydrogen and $C_1$–$C_{20}$ alky.

3. The compound of claim 2, wherein each of $R^1$, $R^2$, and $R^3$ is independently selected from the group consisting of hydrogen, methyl, ethyl, butyl, benzyl, hexyl, cyclohexylmethyl, octyl, and dodecyl.

4. The compound of claim 3, wherein $R^1$, $R^2$, and $R^3$ are H.

5. The compound of claim 1, wherein a is 10 or 12.

6. The compound of claim 5, wherein a is 12.

7. The compound of claim 6, wherein b is 0 and c is 11.

8. A compound comprising a fluorinated polyhedral borate monoanion of the formula $[R^1R^2R^3N—B_{12}H_bF_c]^{-1}$, wherein $R^1$, $R^2$, and $R^3$ are bonded to N, and N is bonded to boron, and each of H and F is bonded to a different boron atom, and wherein
   each of $R^1$, $R^2$, and $R^3$ is independently selected from the group consisting of hydrogen, $C_1$–$C_{20}$ alkyl, $C_3$–$C_{10}$ cycloalkyl, $C_6$–$C_{20}$ aryl, $C_7$–$C_{20}$ aralkyl, haloalkyl, alkenyl, polymer and silyl;
   b is an integer from 0 to 10; and
   c is an integer from 1 to 11; provided the sum of 1+b+c is 12.

9. The compound of claim 8, wherein each of $R^1$, $R^2$, and $R^3$ is independently selected from the group consisting of hydrogen and $C_1$–$C_{20}$ alkyl.

10. The compound of claim 9, wherein each of $R^1$, $R^2$, and $R^3$ is independently selected from the group consisting of hydrogen, methyl, ethyl, butyl, benzyl, hexyl, cyclohexylmethyl, octyl, and dodecyl.

11. The compound of claim 10, wherein $R^1$, $R^2$, and $R^3$ are H.

12. A method for producing a compound of the formula $M[H_3N—B_aH_bF_c]_x$, wherein nitrogen is bonded to boron, and each of H and F is bonded to a different boron atom, said method comprising the steps of contacting an aminohydroborate compound of the formula $M[H_3N—B_aH_{(a-1)}]_x$ with a mixture of HF and $F_2$ to produce said compound of the formula $M[H_3N—B_aH_bF_c]_x$; wherein
   M is a cation;
   x is an integer from 1 to 4;
   a is an integer from 6 to 14;
   b is an integer from 0 to 12; and
   c is an integer from 1 to 13, provided the sum of 1+b+c is a.

13. The method of claim 12, wherein M is cesium.

14. The method of claim 12, wherein a is 10 or 12.

15. The method of claim 14, wherein a is 12.

16. The method of claim 15, wherein b is 0 and c is 11.

17. The method of claim 12 fturther comprising the steps of contacting said compound of the formula $M[H_3N—B_aH_bF_c]_x$ with $R^1$–$X^1$ to produce a monoalkyl aminoborate compound of the formula $M[R^1H_2N—B_aH_bF_c]_x$, wherein
   $X^1$ is a leaving group; and
   $R^1$ is $C_1$–$C_{20}$ alkyl, $C_3$–$C_{10}$ cycloa;kyl, $C_6$–$C_{20}$ aryl, $C_7$–$C_{20}$ aralkyl, an amine protecting group, haloalkyl, alkenyl, polymer or silyl.

18. The method of claim 17 further comprising the steps of contacting said monoalkyl aminoborate compound of the formula $M[R^1H_2N—B_aH_bF_c]_x$ with $R^2$–$X^2$ to produce a dialkyl aminoborate compound of the formula $M[R^1R^2HN—B_aH_bF_c]_x$, wherein
   $X^2$ is a leaving group; and
   $R^2$ is $C_1$–$C_{20}$ alkyl, $C_3$–$C_{10}$ cycloalkyl, $C_6$–$C_{20}$ aryl, $C_7$–$C_{20}$ aralkyl, an amine protecting group, haloalkyl, alkenyl, polymer or silyl.

19. The method of claim 18 further comprising the steps of contacting said dialkyl aminoborate compound of the formula $M[R^1R^2HN-B_aH_bF_c]_x$ with $R^3-X^3$ to produce a trialkyl aminoborate compound of the formula $M[R^1R^2N-B_aH_bF_c]_x$, wherein X$^3$ is a leaving group; and $R^3$ is $C_1-C_{20}$ alkyl, $C_3-C_{10}$ cycloalkyl, $C_6-C_{20}$ aryl, $C_7-C_{20}$ aralkyl, an amine protecting group, haloalkyl, alkenyl, polymer or silyl.

20. The method of claim 19, wherein each of $R^1$, $R^2$, and $R^3$ is independently selected from the group consisting of methyl, ethyl, butyl, benzyl, hexyl, cyclohexylmethyl, octyl, dodecyl.

21. A method for producing an alkylated fluorinated aminoborate compound of the formula $M[R^1R^2R^3N-B_aH_bF_c]_x$, wherein $R^1$, $R^2$ and $R^3$ are bonded to N, and N is bonded to boron, and each of H and F is bonded to a different boron atom, said method comprising the steps of:

(a) contacting an aminohydroborate compound of the formula $M[H_3N-B_aH_{(a-1)}]_x$ with a mixture of HF and $F_2$ to produce a fluorinated aminoborate compound of the formula $M[H_3N-B_aH_bF_c]_x$; and (b) alkylating said fluorinated aminoborate compound with at least one alkylating agent to produce said alkylated fluorinated aminoborate compound, wherein $R^1$ is selected from the group consisting of $C_1-C_{20}$ alkyl, $C_3-C_{10}$ cycloalkyl, $C_6-C_{20}$ aryl, $C_7-C_{20}$ aralkyl, haloalkyl, alkenyl, polymer and silyl;

each of $R^2$, and $R^3$ is independently selected from the group consisting of hydrogen, $C_1-C_{20}$ alkyl, $C_3-C_{10}$ cycloalkyl, $C_6-C_{20}$ aryl, $C_7-C_{20}$ aralkyl, haloalkyl, alkenyl, polymer, and silyl;

M is a cation;

x is an integer from 1 to 4;

a is an integer from 6 to 14;

b is an integer from 0 to 12; and c is an integer from 1 to 13, provided the sum of 1+b+c is a.

22. The method of claim 21, wherein M is cesium.

23. The method of claim 21, wherein a is 10 or 12.

24. The method of claim 23, wherein a is 12.

25. The method of claim 24, wherein b is 0 and c is 11.

26. The method of claim 21, wherein $R^1$ is selected from the group consisting of methyl, ethyl, butyl, benzyl, hexyl, cyclohexylmethyl, octyl, and dodecyl.

27. The method of claim 26, wherein each of $R^2$ and $R^3$ is independently selected from the group consisting of hydrogen, methyl, ethyl, butyl, benzyl, hexyl, cyclohexylmethyl, octyl, and dodecyl.

* * * * *

UNITED STATES PATENT AND TRADEMARK OFFICE
CERTIFICATE OF CORRECTION

PATENT NO.    : 6,335,466 B1
DATED         : January 1, 2002
INVENTOR(S)   : Steven H. Strauss and Sergei V. Ivanov It is certified that error appears in the above-identified patent and that said Letters Patent is hereby corrected as shown below:

Column 2,
Line 17, the "polymeinc" should read -- polymeric --.
Line 25, the "a." should read -- a.) --.
Lines 46-47, the "provides a multiple" should read -- provides multiple --.

Column 3,
Line 3, the "sulflur" should read -- sulfur --.
Line 17, the "fuiran" should read -- furan --.

Column 4,
Line 54, the "chemnical" should read -- chemical --.

Column 5,
Line 18, the "formyliumn" should read -- formylium --.

Column 6,
Line 6, the "usefuil" should read -- useful --.
Line 11, the "having a various" should read -- having various --.

Column 7,
Line 15, the "Seefor" should read -- See for --.

Column 9,
Line 10, the "Monele" should read -- Monel® --.
Line 18, the "reactionto" should read -- reaction to --.
Line 21, the "significantly due to because of the" should read -- significantly due to the --.

Column 10,
Line 12, the "present inventor" should read -- present inventors --.
Line 48, the "olefm" should read -- olefin --.

Column 11,
Line 14, the "vinylidenenorbomene" should read -- vinylidenenorbornene --.
Line 26, the "olefm" should read -- olefin --.
Line 35, the "from about about" should read -- from about --.

Column 12,
Line 15, the "and;" should read -- and --.
Line 23, the "$^{11}B_{=}$-12 to -24" should read -- $^{11}B=$ -12 to -24 --.
Line 38, the "mnL" should read -- mL --.

UNITED STATES PATENT AND TRADEMARK OFFICE
CERTIFICATE OF CORRECTION

PATENT NO. : 6,335,466 B1
DATED : January 1, 2002
INVENTOR(S) : Steven H. Strauss and Sergei V. Ivanov It is certified that error appears in the above-identified patent and that said Letters Patent is hereby corrected as shown below:

<u>Column 13,</u>
Line 1, the "numol" should read -- mmol --.
Line 20, the "rotated for from" should read -- rotated from --.

<u>Column 15,</u>
Line 26, the "an" should read -- and --.
Line 55, the "$Bu_2HNB_{12}F_{11}^{-2}$" should read -- $Bu_2HNB_{12}F_{11}^{-1}$ --.

<u>Column 17,</u>
Line 61, the "refiuxing" should read -- refluxing --.

<u>Column 19,</u>
Line 7, the "nmL" should read -- mL --.
Line 14, the "ofthe" should read -- of the --.
Line 37, the "nmmol" should read -- mmol --.

<u>Column 23,</u>
Line 10, the "nmnol" should read -- mmol --.

<u>Column 24,</u>
Line 48, the "Hoffiman" should read -- Hoffman --.

<u>Column 25,</u>
Line 39, the "2.[001b]" should read -- 2 --.
Line 41, the "$Li(R_xH_{(3-x)}NB_{12}F_{11})$" should read -- $Li(R_xH_{(3-x)}NB_{12}F_{11})$ --.

<u>Column 26,</u>
Line 43, the "suggeests" should read -- suggests --.

<u>Column 27,</u>
Line 31, the "ZfNe" should read -- ZfMe --.
Line 33, the "$ZNe_2$" should read -- $ZMe_2$ --.
Line 62, the "ZpMe2" should read -- $ZpMe_2$ --.

<u>Columns 27-28,</u>
Line 22, the equation "$ZpMe(H_{x3}NB_{12}F_{11}^{-1}) + ZpMe_2 \rightleftharpoons MeZp - Me - ZpMe]^{+1} + H_{x3}NB_{12}F_{11}^{-1}$" should read -- $ZpMe(Hx_3NB_{12}F_{11}^{-1}) + ZpMe_2 \rightleftharpoons [MeZp - Me - ZpMe]^{+1} + Hx_3NB_{12}F_{11}^{-1}$ --

UNITED STATES PATENT AND TRADEMARK OFFICE
CERTIFICATE OF CORRECTION

PATENT NO. : 6,335,466 B1
DATED : January 1, 2002
INVENTOR(S) : Steven H. Strauss and Sergei V. Ivanov It is certified that error appears in the above-identified patent and that said Letters Patent is hereby corrected as shown below:

Column 28,
Line 1, the "ion-pairing coordination)" should read -- ion-pairing (i.e., stronger coordination) --.
Line 12, the "regonnee" should read -- resonance --.
Line 12, the "fluonl" should read -- fluorine --.
Line 32, the "5%" should read -- ~5% --.
Line 34, the "~50%)" should read -- ~50% --.

Column 29,
Line 9, "NBu$_3$H$_{+1}$" should read -- NBu$_3$H$^{+1}$ --.
Line 46, the "puftatively" should read -- putatively --.

Column 30,
Line 51, the "H3NB12F11-, and 1-H-CB11F11-" should read -- H$_3$NB$_{12}$F$_{11}$-, and 1-H-CB$_{11}$F$_{11}$- --.
Line 55, the "NH$_2$Ph$^{+1}$" should read -- NH$_3$Ph$^{+1}$ --.
Line 57, the "HCO$_3$" should read -- HCO$_3^{-1}$ --.
Line 59, the "NH3Bu$^{+1}$" should read -- NH$_3$Bu$^{+1}$ --.

Column 31,
Line 8, the "I" should read -- 1 --.
Line 57, the "tbennally" should read -- thermally --.
Lines 57-58, the "Methylliium" should read -- Methyllithium --.
Line 58, the "aiethyl" should read -- diethyl --.

Column 32,
Line 16, the "dimethyizirconecene" should read -- dimethylzirconecene --.
Line 64, the "as" should read -- was --.
Line 64, the "flrther" should read -- further --.

Column 33,
Line 53, the "alky" should read -- alkyl --.

UNITED STATES PATENT AND TRADEMARK OFFICE
CERTIFICATE OF CORRECTION

PATENT NO. : 6,335,466 B1
DATED : January 1, 2002
INVENTOR(S) : Steven H. Strauss and Sergei V. Ivanov It is certified that error appears in the above-identified patent and that said Letters Patent is hereby corrected as shown below:

<u>Column 34,</u>
Line 56, the "cycloa;kyl" should read -- cycloalkyl --.

<u>Column 35,</u>
Lines 4-5, the "$M[R^1R^2N-B_aH_bF_c]_x$" should read -- $M[R^1R^2R^3N-B_aH_bF_c]_x$ --.
Line 11, the "$R^3$is" should read -- $R^3$ is --.

Signed and Sealed this

Nineteenth Day of November, 2002

*Attest:*

JAMES E. ROGAN
*Attesting Officer*   *Director of the United States Patent and Trademark Office*